(12) United States Patent
Hicks et al.

(10) Patent No.: US 12,234,510 B2
(45) Date of Patent: *Feb. 25, 2025

(54) VARIETAL COUNTING OF NUCLEIC ACIDS FOR OBTAINING GENOMIC COPY NUMBER INFORMATION

(71) Applicant: Cold Spring Harbor Laboratory, Cold Spring Harbor, NY (US)

(72) Inventors: James Hicks, Locust Valley, NY (US); Nicholas Navin, Houston, TX (US); Jennifer Troge, Oyster Bay, NY (US); Zihua Wang, Huntington, NY (US); Michael Wigler, Cold Spring Harbor, NY (US)

(73) Assignee: COLD SPRING HARBOR LABORATORY, Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/269,818

(22) Filed: Feb. 7, 2019

(65) Prior Publication Data

US 2019/0153535 A1    May 23, 2019

Related U.S. Application Data

(63) Continuation of application No. 15/063,278, filed on Mar. 7, 2016, which is a continuation of application No. 13/278,333, filed on Oct. 21, 2011, now Pat. No. 9,404,156.

(60) Provisional application No. 61/510,579, filed on Jul. 22, 2011, provisional application No. 61/406,067, filed on Oct. 22, 2010.

(51) Int. Cl.
| | | |
|---|---|---|
| C12P 19/34 | (2006.01) | |
| C12Q 1/683 | (2018.01) | |
| C12Q 1/6874 | (2018.01) | |
| C12Q 1/6881 | (2018.01) | |
| C12Q 1/6886 | (2018.01) | |
| G16B 25/00 | (2019.01) | |

(52) U.S. Cl.
CPC ........... *C12Q 1/6874* (2013.01); *C12Q 1/683* (2013.01); *C12Q 1/6881* (2013.01); *C12Q 1/6886* (2013.01); *G16B 25/00* (2019.02); *C12Q 2600/156* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | |
|---|---|---|
| 5,639,603 A | 6/1997 | Dower |
| 6,013,445 A | 1/2000 | Albrecht |
| 6,172,214 B1 | 1/2001 | Brenner |
| 6,569,617 B1 | 5/2003 | Wigler |
| 7,531,307 B2 | 5/2009 | Wigler |
| 7,537,897 B2 | 5/2009 | Brenner |
| 7,622,281 B2 | 11/2009 | Ronaghi |
| 7,700,324 B1 | 4/2010 | Issa |
| 8,273,871 B2 | 9/2012 | Hannon |
| 8,554,488 B2 | 10/2013 | Wigler |
| 8,663,917 B2 | 3/2014 | Wigler |
| 8,694,263 B2 | 4/2014 | Wigler |
| 8,715,967 B2 * | 5/2014 | Casbon ................. G16B 20/10 435/6.12 |
| 8,741,606 B2 | 6/2014 | Casbon |
| 9,404,156 B2 | 8/2016 | Hicks |
| 9,476,095 B2 | 10/2016 | Vogelstein |
| 9,487,829 B2 | 11/2016 | Vogelstein |
| 9,670,536 B2 | 6/2017 | Casbon |
| 10,947,589 B2 * | 3/2021 | Hicks ..................... C12Q 1/683 |
| 2004/0110153 A1 | 6/2004 | Dong |
| 2005/0032095 A1 | 2/2005 | Wigler |

(Continued)

FOREIGN PATENT DOCUMENTS

| | | |
|---|---|---|
| DE | 10 2008 025 656 A1 | 12/2009 |
| WO | WO 2007/062445 | 6/2007 |
| WO | WO 2012/054873 | 4/2012 |

OTHER PUBLICATIONS

"Mutational load". printed on Mar. 26, 2021.*
McInerney et al., Error Rate Comparison during Polymerase Chain Reaction by DNA Polymerase. Molecular Biology International, Article ID 287430, Aug. 17, 2014.*
Xie et al., CNV-seq, a new method to detect copy number variation using high-throughput sequencing. BMC Bioinformatics, 10, 80, Mar. 6, 2009.*
Jun. 26, 2012 International Search Report issued in connection with PCT International Application No. PCT/US2011/057350 (WO 2012/054873).

(Continued)

*Primary Examiner* — Frank W Lu
(74) *Attorney, Agent, or Firm* — Gary J. Gershik

(57) ABSTRACT

A method for obtaining from genomic material genomic copy number information unaffected by amplification distortion, comprising obtaining segments of the genomic material, tagging the segments with substantially unique tags to generate tagged nucleic acid molecules, such that each tagged nucleic acid molecule comprises one segment of the genomic material and a tag, subjecting the tagged nucleic acid molecules to polymerase chain reaction (PCR) amplification, generating tag associated sequence reads by sequencing the product of the PCR reaction, assigning each tagged nucleic acid molecule to a location on a genome associated with the genomic material by mapping the subsequence of each tag associated sequence read corresponding to a segment of the genomic material to a location on the genome, and counting the number of tagged nucleic acid molecules assigned to the same location on the genome having a different tag, thereby obtaining genomic copy number information unaffected by amplification distortion.

36 Claims, 15 Drawing Sheets
(15 of 15 Drawing Sheet(s) Filed in Color)
Specification includes a Sequence Listing.

(56) References Cited

U.S. PATENT DOCUMENTS

| | | |
|---|---|---|
| 2005/0214812 A1* | 9/2005 | Li .................. C12Q 1/6827 435/6.12 |
| 2005/0266444 A1 | 12/2005 | Wigler |
| 2006/0035258 A1 | 2/2006 | Tadakamalla |
| 2006/0073506 A1 | 4/2006 | Christians |
| 2007/0020640 A1 | 1/2007 | McCloskey |
| 2007/0031857 A1* | 2/2007 | Makarov ............ C12N 15/1068 435/6.1 |
| 2007/0172873 A1 | 7/2007 | Brenner |
| 2007/0207481 A1 | 9/2007 | Wigler |
| 2008/0261204 A1 | 10/2008 | Lexow |
| 2009/0137402 A1 | 5/2009 | Wang |
| 2010/0178655 A1 | 7/2010 | Hamilton |
| 2010/0203538 A1 | 8/2010 | Dube |
| 2010/0227768 A1 | 9/2010 | Wigler |
| 2012/0149593 A1 | 6/2012 | Hicks |
| 2012/0328607 A1 | 12/2012 | Hicks |
| 2013/0179999 A1 | 7/2013 | Hannon |
| 2014/0025307 A1 | 1/2014 | Wigler |
| 2016/0215333 A1 | 7/2016 | Vogelstein |
| 2016/0251715 A1 | 9/2016 | Hicks |
| 2017/0051347 A1 | 2/2017 | Vogelstein |

OTHER PUBLICATIONS

Apr. 23, 2013 International Preliminary Report on Patentability issued in connection with PCT International Application No. PCT/US2011/057350 (WO 2012/054873).

Feb. 13, 2014 Extended European Search Report, issued in connection with European Patent Application No. 11835243.4.

Nov. 20, 2015 Communication under Rule 94(3) EPC issued by the European Patent Office in connection with European Patent Application No. 11835243.4.

Jun. 27, 2016 Amendment under Rule 94(3) EPC to Nov. 20, 2015 Communication under Rule 94(3) EPC issued by the European Patent Office in connection with European Patent Application No. 11835243.4.

Oct. 9, 2017 Communication under Rule 71(3) EPC issued by the European Patent Office in connection with European Patent Application No. 11835243.4.

Feb. 16, 2018 Amendment under Rule 71(3) EPC to Oct. 9, 2017 Communication under Rule 71(3) EPC issued by the European Patent Office in connection with European Patent Application No. 11835243.4.

Notice of Opposition to a European Patent, filed Jan. 25, 2019 by Opponent, James Poole Limited, with European Patent Office, concerning European Patent No. EP 2630263.

Communication of a Notice of Opposition, issued by the European Patent Office on Feb. 1, 2019, concerning European Patent No. EP2630263.

Dec. 8, 2017 Office Action issued by the Canadian Intellectual Property Office in connection with Canadian Patent Application 2,815,076.

May 3, 2016 Patent Examination Report No. 1 issued by IP Australia in connection with Australian Patent Application 2011316807.

Apr. 19, 2017 Response to May 3, 2016 Patent Examination Report No. 1 issued by IP Australia in connection with Australian Patent Application 2011316807.

Apr. 20, 2017 Patent Examination Report No. 2 issued by IP Australia in connection with Australian Patent Application 2011316807.

May 2, 2017 Response to Apr. 20, 2017 Patent Examination Report No. 2 issued by IP Australia in connection with Australian Patent Application 2011316807.

Sep. 7, 2017 Notice of Grant for Patent issued by IP Australia in connection with Australian Patent Application 2011316807.

Casbon et al., "A method for counting PCT template molecules with application to next-generation sequencing", Nucleic Acids Res. vol. 39 No. 12 (Jul. 2011).

Castle et al., "DNA copy number, including telomeres and mitochondria, assayed using next-generation sequencing," BMC Genomics vol. 11 No. 244 (2010).

Cheung V.G. & Nelson S.F., "Whole genome amplification using a degenerate oligonucleotide primer allows hundreds of genotypes to be performed on less than one nanogram of genomic DNA," PNAS vol. 93 No. 25 (Dec. 1996), p. 14676-14679.

Chiang et al., "High-Resolution Mapping of Copy Number Alterations with Massively Parallel Sequencing," Nature Methods, vol. 6 No. 1 (2008), p. 99-103.

Craig et al., "Identification of Genetic Variants Using Bar-coded Multiplexed Sequencing," Nature Methods, vol. 5 No. 10 (Oct. 2008), p. 887-893.

Eid et al., "Real-Time DNA Sequencing from Single Polymerase Molecules," Science vol. 323 No. 5910 (Jan. 2009), p. 133-138.

Supporting Online Material for Eid et al., "Real-Time DNA Sequencing from Single Polymerase Molecules," accessible at www.sciencemag.org/cgi/content/full/1162986/DC1, (published Nov. 20, 2008).

Fu G.K. et al., "Counting individual DNA molecules by the stochastic attachment of diverse labels," PNAS vol. 108 No. 22 (May 2011), p. 9026-9031.

Hiatt et al., "Parallel, tag-directed assembly of locally derived short sequence reads," Nature Methods, vol. 7 No. 2 (2010), p. 119-122.

Hug & Schuler, "Measurement of the Number of Molecules of a Single mRNA Species in a Complex mRNA Preparation," J. Theor. Biol., vol. 221 (2003), p. 615-624.

Islam et al., "Characterization of the single-cell transcriptional landscape by highly multiplex RNA-seq," Genome Res. vol. 21 No. 7 (Jul. 2011) p. 1160-1167.

Kivioja et al., Counting absolute numbers of molecules using unique molecular identifiers, Nature Methods vol. 9 (2012), p. 72-74.

McCloskey M.L. et al, "Encoding PCR Products with Batch-stamps and Barcodes," Biochem. Genet. vol. 45 (Dec. 2007), p. 761-767.

Miner et al., "Molecular barcodes detect redundancy and contamination in hairpin-bisulfite PCR," Nucleic Acids Res. vol. 32 No. 17 (2004), p. 1-4.

Meyerson et al., "Advances in Understanding Cancer Genomes Through Second-Generation Sequencing," Nature Reviews, vol. 11 (2010), p. 685-696.

Parameswaran et al., "A pyrosequencing-tailored nucleotide barcode design unveils opportunities for large-scale sample multiplexing," Nucleic Acids Res. vol. 35 No. 19 (2007).

Paunio T. et al., "Preimplantation diagnosis by whole genome amplification, PCT amplification, and solid-phase minisequencing of blastomere DNA," Clinical Chem. vol. 42 No. 9 (1996), p. 1382-1390.

Plessy et al., "Linking promoters to functional transcripts in small samples with nanocage and CAGEscan," Nature Methods, vol. 7 No. 7 (2010), p. 528-534.

Shiroguchi at al., "Digital RNA sequencing minimizes sequence-dependent bias and amplification noise with optimized single-molecule barcodes," PNAS vol. 109 No. 4 (2012), p. 1347-1352.

Technology Backgrounder: Single Molecule Real Time (SMRTTM) DNA Sequencing, Pacific Bioscience (2009).

Aug. 20, 2019 Response to Opposition including Main Request and Auxiliary Requests 1-5 filed with the European Patent Office by Patentee Cold Spring Harbor Laboratory in connection with European Patent No. EP 2630263.

Sep. 26, 2019 Provisional and Non-Binding Opinion of the Opposition Division issued in connection with European Patent No. EP 2630263.

Nov. 7, 2019 Reply to the Provisional and Non-Binding Opinion of the Oppositon Division including Corrected Auxiliary Requests 1, 3, and 5 filed with the European Patent Office by Patentee Cold Spring Harbor Laboratory in connection with European Patent No. EP 2630263.

Mar. 3, 2020 Submissions from the Opponent in accordance with Rule 116 EPC filed by Opponent James Poole Limited in connection with European Patent No. EP 2630263.

(56) References Cited

OTHER PUBLICATIONS

Wang, Tian-Li, et al. "Digital karyotyping." Proceedings of the National Academy of Sciences 99, No. 25 (Dec. 10, 2002): 16156-16161.

Jan. 15, 2021 Patent Proprietor's final written submissions in accordance with Rule 116 EPC filed in connection with European Patent No. EP 2630263.

Linnarsson, Sten. "Recent advances in DNA sequencing methods—general principles of sample preparation." Experimental cell research 316, No. 8 (2010): 1339-1343.

Mar. 17, 2021 Information regarding the result of oral proceedings in connection with European Patent No. EP 2630263.

May 6, 2021 Interlocutory decision in Opposition proceedings (Art. 101(3)(a) and 106(2) EPC issued by the Opposition Division in connection with European Patent No. EP 2630263.

May 7, 2021 Office Action issued in connection with Canadian Patent Application No. 3,080,686.

Sep. 7, 2021 Response to May 7, 2021 Office Action filed in connection with Canadian Patent Application No. 3,080,686.

Apr. 30, 2024 extended European search report issued in connection with European Patent Application No. 23197909.7.

* cited by examiner

Fig. 7B (continued from Fig. 7A)
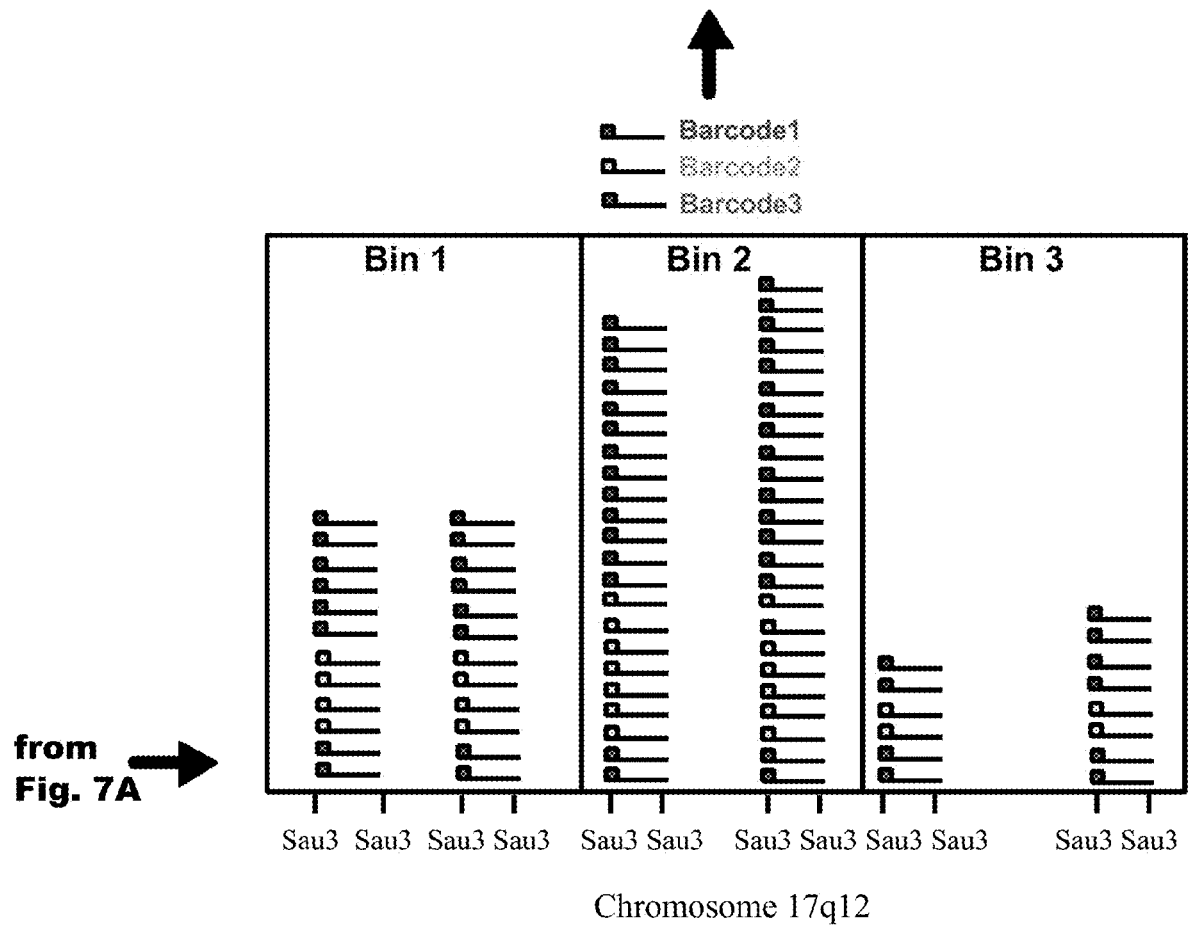

Fig. 7C (continued from Fig. 7B)

RepSeq Barcoding
(whole genome copy number analysis of many single tumor cells)

RepSeq Barcode Bin Data

Bin1
Barcode 1 Mean Copy Number = 6
Barcode 2 Mean Copy Number = 4
Barcode 3 Mean Copy Number = 2

Bin2
Barcode 1 Mean Copy Number = 14
Barcode 2 Mean Copy Number = 7
Barcode 3 Mean Copy Number = 2

Bin3
Barcode 1 Mean Copy Number = 3
Barcode 2 Mean Copy Number = 2
Barcode 3 Mean Copy Number = 2

from Fig. 7B

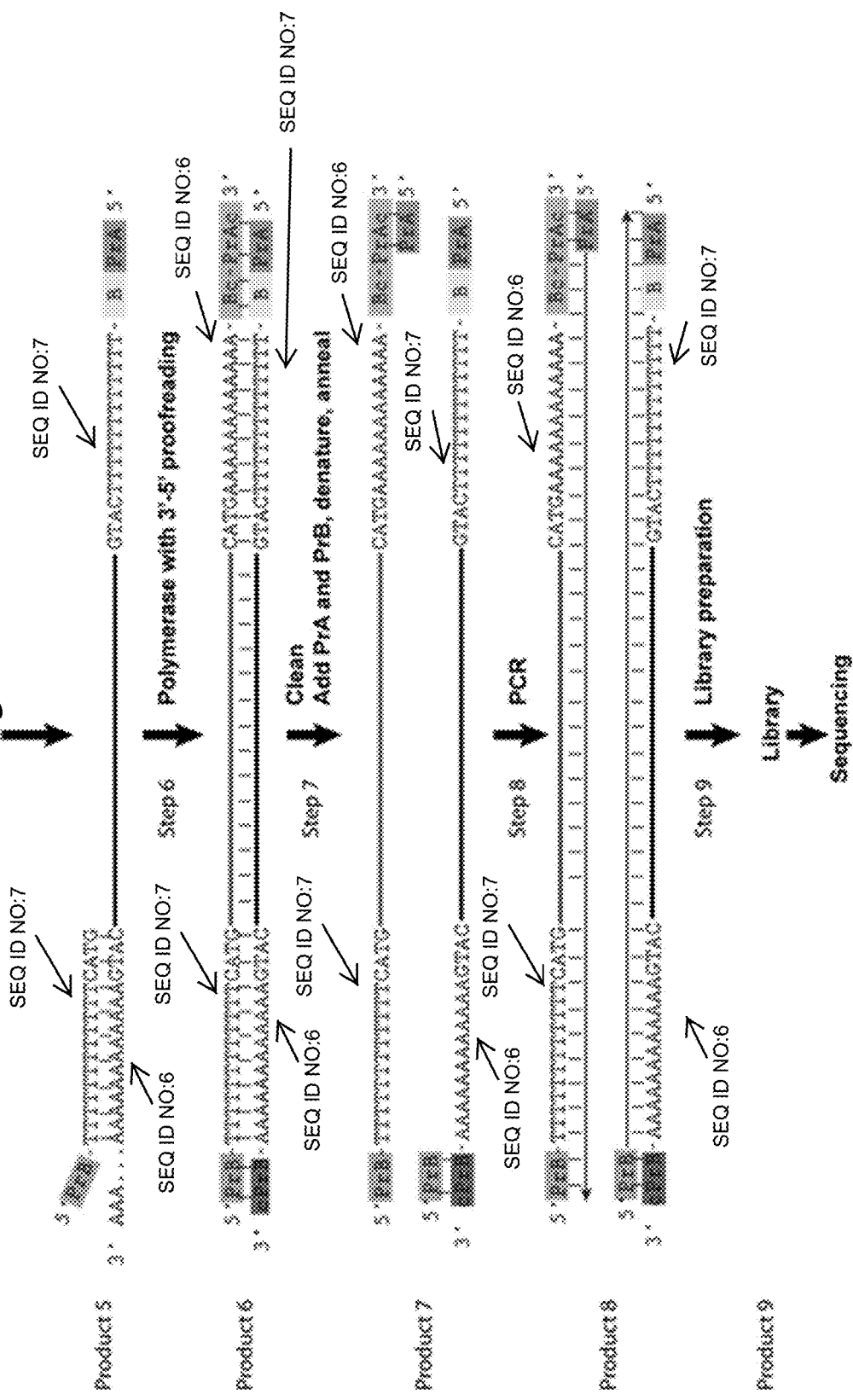
Fig. 9B (continued from Fig. 9A)

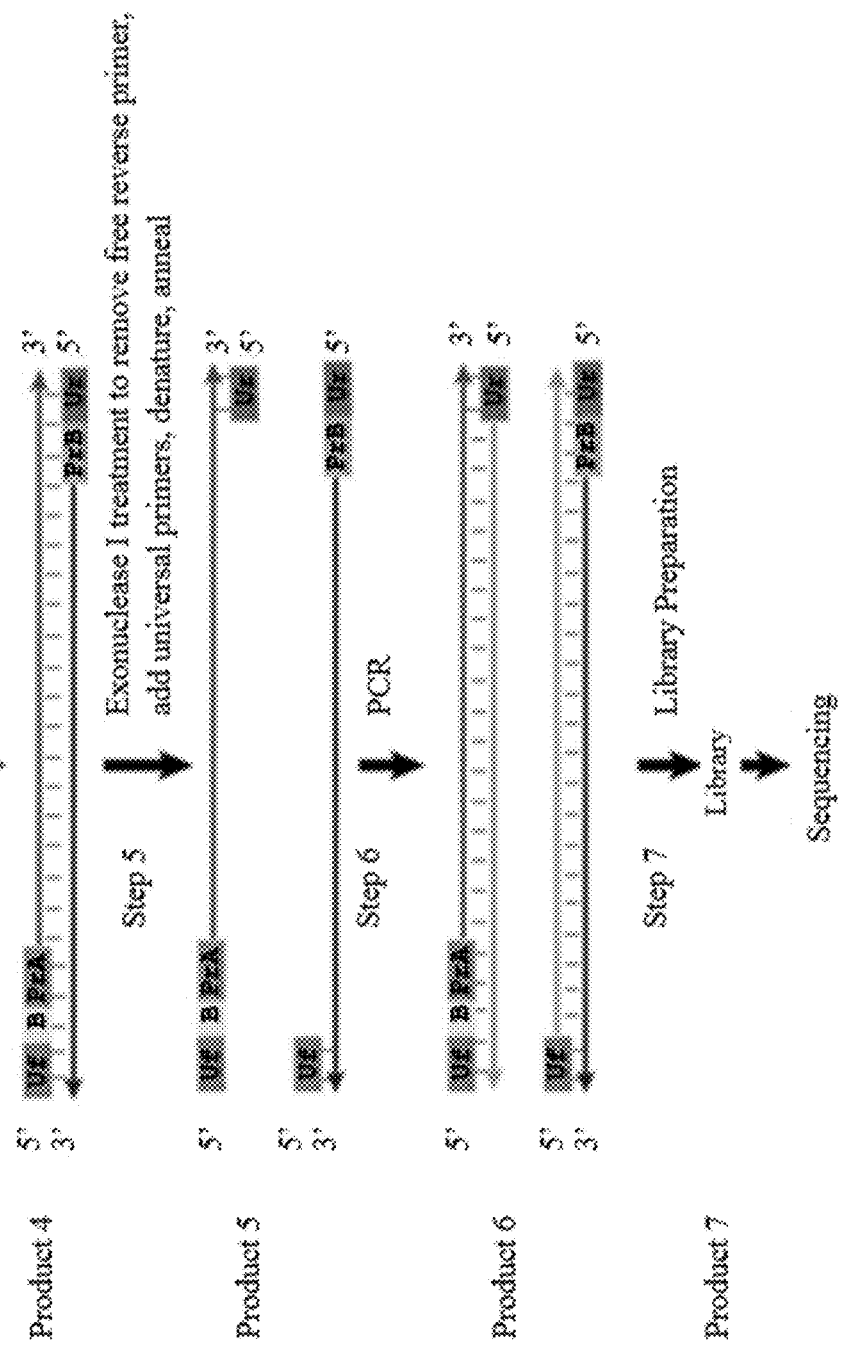
Fig. 10B
(continued from Fig. 10A)

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Portion of 3' end of nucleotide sequence after
      Terminal Transferase step

<400> SEQUENCE: 1
catgaaaaaa aaaaa                                                         15

<210> SEQ ID NO 2
<211> LENGTH: 24
```

```
<212> TYPE: DNA
<213> ORGANISM: Artificial Sequence
<220> FEATURE:
<223> OTHER INFORMATION: Nucleotide sequence comprising a sequence
      complementary to portion of 3' end of a nucleotide sequence, and a
      varietal tag
<220> FEATURE:
<221> NAME/KEY: misc_feature
<222> LOCATION: (1)..(10)
<223> OTHER INFORMATION: n is a, c, g, or t

<400> SEQUENCE: 2
nnnnnnnnnn tttttttttt catg                                           24

<210> SEQ ID NO 3
<211> LENGTH: 11
<212> TYPE: DNA
<213> ORGANISM: Artificial Sequence
<220> FEATURE:
<223> OTHER INFORMATION: Portion of 3' end of nuceotide sequence after
      Pool, Cleanup, Melt, Terminal Transferase

<400> SEQUENCE: 3
cccccccccc c                                                         11

<210> SEQ ID NO 4
<211> LENGTH: 10
<212> TYPE: DNA
<213> ORGANISM: Artificial Sequence
<220> FEATURE:
<223> OTHER INFORMATION: Portion of a primer complementary to portion of
      3' end of nucleotide sequence

<400> SEQUENCE: 4
gggggggggg                                                           10

<210> SEQ ID NO 5
<211> LENGTH: 12
<212> TYPE: DNA
<213> ORGANISM: Artificial Sequence
<220> FEATURE:
<223> OTHER INFORMATION: Portion of 3' end of nucleotide sequence after
      Terminal Transferase step

<400> SEQUENCE: 5
catgaaaaaa aa                                                        12

<210> SEQ ID NO 6
<211> LENGTH: 16
<212> TYPE: DNA
<213> ORGANISM: Artificial Sequence
<220> FEATURE:
<223> OTHER INFORMATION: Portion of 3' end of nucleotide sequence after
      Terminal Transferase step

<400> SEQUENCE: 6
catgaaaaaa aaaaaa                                                    16

<210> SEQ ID NO 7
<211> LENGTH: 16
<212> TYPE: DNA
<213> ORGANISM: Artificial Sequence
<220> FEATURE:
<223> OTHER INFORMATION: Portion of primer complementary to portion of
      3' end of nucleotide sequence

<400> SEQUENCE: 7
tttttttttt ttcatg                                                    16
```

```
<210> SEQ ID NO 8
<211> LENGTH: 14
<212> TYPE: DNA
<213> ORGANISM: Artificial Sequence
<220> FEATURE:
<223> OTHER INFORMATION: Portion of 3' end of nucleotide segment after
      Terminal Transferase step

<400> SEQUENCE: 8
catgaaaaaa aaaa                                                        14
```

VARIETAL COUNTING OF NUCLEIC ACIDS FOR OBTAINING GENOMIC COPY NUMBER INFORMATION

This application is a continuation of U.S. Ser. No. 15/063,278, filed Mar. 7, 2016, now U.S. Pat. No. 10,947,589, issued Feb. 24, 2021, which is a continuation of U.S. Ser. No. 13/278,333, filed Oct. 21, 2011, now U.S. Pat. No. 9,404,156, issued Aug. 2, 2013, which claims the benefit of U. S. Provisional Application Nos. 61/510,579, filed Jul. 22, 2011, and 61/406,067, filed Oct. 22, 2010 the contents of each of which are hereby incorporated by reference in their entirety into this application.

This invention was made with government support under grant W81XWH-09-1-0591. The Government has certain rights in the invention.

Throughout this application, various publications are referenced by numbers in parentheses. Full citations for these references may be found at the end of the specification immediately preceding the claims. The disclosures of these publications in their entireties are hereby incorporated by reference into this application to more fully describe the state of the art to which this invention pertains.

REFERENCE TO A SEQUENCE LISTING

This application incorporates-by-reference nucleotide and/or amino acid sequences which are present in the file named "190207_81503AAA_Sequence_Listing_ADR.txt" which is 2.59 kilobytes in size, and which was created Feb. 7, 2019 in the IBM-PC, machine format, having an operating system compatibility with MS-Windows, which is contained in the text file filed Feb. 7, 2019 as part of this application.

BACKGROUND OF THE INVENTION

Genomic copy number information is commonly obtained using whole genome amplification (WGA). The endemic problem with the WGA method is over-sampling of certain regions, yielding a non-uniform amplification of the genome (1). WGA methods begin with the step that initiates the process, a polymerase (Phi 29) makes a strand from genomic DNA utilizing a random primer coupled to an adaptor for subsequent PCR (FIG. 1). If the input DNA strands are referred to as the "0-th derivative", and the first synthesized strand as a "first derivative," subsequent strands are called the (n+1)-th derivative if their template was an n-th derivative. Only strands that are 2-nd derivative or higher become amplified in the PCR step, resulting in a 'stacking' over the regions 'chosen' by the polymerase for the first derivative.

Coverage of the genome by sequencing WGA of single cell DNA is limited by the stacking phenomenon (FIG. 2). Thus it is difficult to obtain single cell measurements, particularly when based on WGA, due to distortions that originate from stochastic sampling and amplification steps. Moreover, the current method of WGA is a black box, with the unspecified reagents purchased from a vendor, which hampers optimization. Moreover, the WGA method does not extend to a method usable for single cell RNA profiling.

Ligation-mediated PCR was developed in an attempt to solve the above-identified problems inherent in WGA. In this method, adaptors are ligated to an MseI restriction endonuclease digest of genomic DNA from a single cell, followed by PCR amplification using primers complementary to the adaptors. The amplified DNA is then used for CGH or DNA sequencing (2,3). However, like WGA, the method still requires an amplification step.

Parameswaran et. al. (2007) and U.S. Pat. No. 7,622,281 describe methods of labeling nucleic acid molecules with barcodes for the purpose of identifying the source of the nucleic acid molecules, thereby allowing for high-throughput, sequencing of multiple samples (4,5). Eid et. al. (2009) describe a single molecule sequencing method wherein single-molecule real time sequencing data is obtained from a DNA polymerase performing uninterrupted template-directed synthesis using four distinguishable fluorescently labeled dNTPs (6). However, these methods do not provide genomic information unaffected by amplification distortion.

Miner et al. (2004) describe a method of molecular barcoding to label template DNA prior to PCR amplification, and report that the method allows for the identification of contaminant and redundant sequences by counting only distinctly tagged sequences (22). U.S. Pat. No. 7,537,897 describes methods for molecular counting by labeling molecules of an input sample with unique oligonucleotide tags and subsequently amplifying and counting the number of different tags (23). Miner et. al. and U.S. Pat. No. 7,537,897 both describe labeling of input nucleic acid molecules by ligation, which has been found to be an inefficient reaction.

McCloskey et al. (2007) describe a method of molecular encoding which does not use ligation but instead uses template specific primers to barcode template DNA molecules prior to PCR amplification (24). However, such a method requires that template specific primers be made for each species of template DNA molecule studied.

As described herein, obtaining accurate genomic copy number information by high-throughput sequencing of genomic DNA prepared by WGA methods is hampered by the copy number distortions introduced by non-uniform amplification of genomic DNA. Thus, there exists a need for a method that allows for copy number determination free oaf distortions caused by amplification steps and which allows for accurate and efficient copy number determination of complex samples. Such a method should also be robust using existing methodologies for high volume, massively parallel sequencing.

SUMMARY OF THE INVENTION

A method is provided for obtaining from genomic material genomic copy number information unaffected by amplification distortion, comprising:
a) obtaining segments of the genomic material;
b) tagging the segments with substantially unique tags to generate tagged nucleic acid molecules, such that each tagged nucleic acid molecule comprises one segment of the genomic material from step (a) and a tag;
c) subjecting the tagged nucleic acid molecules to amplification by polymerase chain reaction (PCR);
d) generating tag associated sequence reads sequencing the product of step (c);
e) assigning each tagged nucleic acid molecule to a location on a genome associated with the genomic material by mapping the subsequence of each tag associated sequence read corresponding to a segment of the genomic material to a location on the genome; and
f) counting the number of tagged nucleic acid molecules having a different tag that have been assigned to the same location on the genome,
thereby obtaining genomic copy number information unaffected by amplification distortion.

Also provided is a method for obtaining from mRNA transcripts mRNA copy number information unaffected by amplification distortion, comprising:

a) obtaining cDNA from the mRNA transcripts;
b) optionally obtaining segments of the cDNA;
c) tagging the cDNA or segments of cDNA with substantially unique tags to generate tagged nucleic acid molecules, such that each tagged nucleic acid molecule comprises
   i) one cDNA from step (a) or one segment of the cDNA from step (b), and
   ii) a tag;
d) subjecting the tagged nucleic acid molecules to amplification by polymerase chain reaction (PCR);
e) generating tag associated sequence reads by sequencing the product of step (d);
f) assigning each tagged nucleic acid molecule to a location on a cDNA library associated with the mRNA transcripts by mapping the subsequence of each tag associated sequence read corresponding to a cDNA or a segment of cDNA to a location on the cDNA library; and
g) counting the number of tagged nucleic acid molecules having a different tag that have been assigned to the same location on the cDNA library,
thereby obtaining mRNA copy number information unaffected by amplification distortion.

Also provided is a method for obtaining from mRNA transcripts mRNA copy number information unaffected by amplification distortion, comprising:
a) generating tagged nucleic acid molecules, comprising:
   i) subjecting the mRNA transcripts to a polymerase reaction in the presence of primers capable of hybridizing to the polyA tail of the mRNA transcripts under conditions that promote the formation of only one complement, thereby generating first order derivative strands;
   ii) adding a polynucleotide tail to the first order derivative strands; and
   iii) subjecting the first order derivative strands to a polymerase reaction in the presence of primers capable of hybridizing to the polynucleotide tail added in step (ii) under conditions that promote the formation of only one complement, thereby generating second order derivative strands,
wherein the primers of at least one of steps (i) and (iii) comprise substantially unique primers, thereby generating tagged nucleic acid molecules;
b) subjecting the tagged nucleic acid molecules to polymerase chain reaction (PCR) amplification;
c) generating tag associated sequence reads by sequencing the product of step (b);
d) assigning each tagged nucleic acid molecule to a location on a cDNA library associated with the mRNA transcripts by mapping the subsequence of each tag associated sequence read corresponding to a mRNA transcript to a location on the cDNA library; and
e) counting the number of tagged nucleic acid molecules having a different tag that have been assigned to the same location on the cDNA library,
thereby obtaining mRNA copy number information unaffected by amplification distortion.

Also provided is a method for obtaining from genomic material DNA methylation information unaffected by amplification distortion, comprising:
a) obtaining segments of the genomic material;
b) adding a polynucleotide tail to the ends of the segments of the genomic material to generate zero-th order derivative strands;
c) subjecting the zero-th order derivative strands to a polymerase reaction in the presence essentially unique primers, wherein the essentially unique primers are capable of hybridizing to the polynucleotide tail of the zero-th order strands, under conditions that promote the formation of only one complement, thereby generating tagged nucleic acid molecules;
d) separating the tagged nucleic acid molecules tagged nucleic acid molecules and a group consisting of unmethylated tagged nucleic acid molecules;
e) subjecting each group of step (d) to amplification by polymerase chain reaction (PCR);
f) generating tag associated sequence reads by sequencing the product of step (e);
g) assigning each tagged nucleic acid molecule to a location on a genome associated with the genomic material by mapping the subsequence of each tag associated sequence read corresponding to a segment of the genomic material to a location on the genome; and
h) counting the number of tagged nucleic acid molecules having a different tag that have been assigned to the same location on the genome,
thereby obtaining DNA methylation information unaffected by amplification distortion.

Also provided is a composition of matter derived from genomic material comprising tagged nucleic acid molecules, said tagged nucleic acid molecules being produced by a process comprising:
a) obtaining segments of the genomic material;
b) adding a polynucleotide tail to the ends of the segments of the genomic material to generate zero-th order derivative strands;
c) subjecting the zero-th order derivative strands of step (b) to a polymerase reaction in the presence of primers capable of hybridizing to the polynucleotide tail of the zero-th order strands under conditions that promote the formation of only one complement, thereby generating first order derivative strands;
d) adding a polynucleotide tail to the first order derivative strands;
e) subjecting the first order derivative strands to a polymerase reaction in the presence of primers capable of hybridizing to the polynucleotide tail of the order derivative strands under conditions that promote the formation of only one complement, thereby generating second order derivative strands,
wherein the primers of at least one of steps (c) and (e) comprise substantially unique primers, thereby generating tagged nucleic acid molecules.

Also provided is a composition of matter derived from genomic material comprising tagged nucleic acid molecules, said tagged nucleic acid molecules being produced by a process comprising:
a) obtaining segments of genomic material;
b) adding a polynucleotide tail to the ends of the segments of genomic material to generate zero-th order derivative strands,
c) subjecting the zero-th order derivative strands of step (b) to a ligation reaction in the presence of primers capable of hybridizing to the polynucleotide tail of the zero-th conditions that promote the ligation of a primer to the 5' ends of the zero-th order derivative strands,
d) subjecting the product of step (c) to a polymerase reaction in the presence of primers capable of hybridizing to the polynucleotide tail added in step (b) under conditions which promote the formation of only one complement, wherein the primers of step (d) have different nucleotide sequences than the primers of step (c), and wherein the polymerase has 3'-5' proofreading activity, wherein the primers of at least one of steps (c) and (d) comprise substantially unique primers, thereby generating tagged nucleic acid molecules.

Also provided is a composition of matter derived from a mRNA transcripts comprising tagged nucleic acid molecules, said tagged nucleic acid molecules being produced by a process comprising:
a) obtaining cDNA from the mRNA transcripts;
b) optionally obtaining segments of the cDNA; and
c) tagging the cDNA or segments of cDNA with substantially unique tags to generate tagged nucleic acid molecules, wherein each tagged nucleic acid molecule comprises
  i) one cDNA from step (a) or one segment of the cDNA from step (b) and
  ii) a tag.

Also provided is a composition of matter derived from mRNA transcripts comprising tagged nucleic acid molecules, said tagged nucleic acid molecules being produced by a process comprising:
a) obtaining mRNA transcripts;
b) subjecting the mRNA transcripts to a polymerase reaction in the presence of primers capable of hybridizing to the polyA tail of the mRNA transcripts under conditions that promote the formation of only one complement, thereby generating first order derivative strands;
c) adding a polynucleotide tail to the first order derivative strands;
d) subjecting the first order derivative strands to a polymerase reaction in the presence of primers capable of hybridizing to the polynucleotide tail added in step (c) under conditions that promote the formation of only one complement, thereby generating second order derivative strands,
wherein the primers of at least one of steps (b) and (d) comprise substantially unique primers, thereby generating tagged nucleic acid molecules.

Also provided is a kit for determining nucleic acid copy number information unaffected by amplification distortion comprising:
a) a terminal transferase, and
b) plurality of substantially unique primers,
wherein the substantially unique primers comprise substantially unique tags, and wherein the substantially unique primers are capable of hybridizing to the polynucleotide tail of a nucleic acid molecule which has a polynucleotide tail added by the terminal transferase.

BRIEF DESCRIPTION OF THE FIGURES

The patent or application file contains at least one drawing executed in color. Copies of this patent or patent application publication with color drawing(s) will be provided by the Office upon request and payment of the necessary fee.

Genomic coverage comparison of 7 sequencing lanes from one single cell library versus 7 lanes from a million cell library. Stacking causes the single cell reads to be concentrated over the first derivative reads from WGA. More reads yield diminishing returns.

Figure 1:
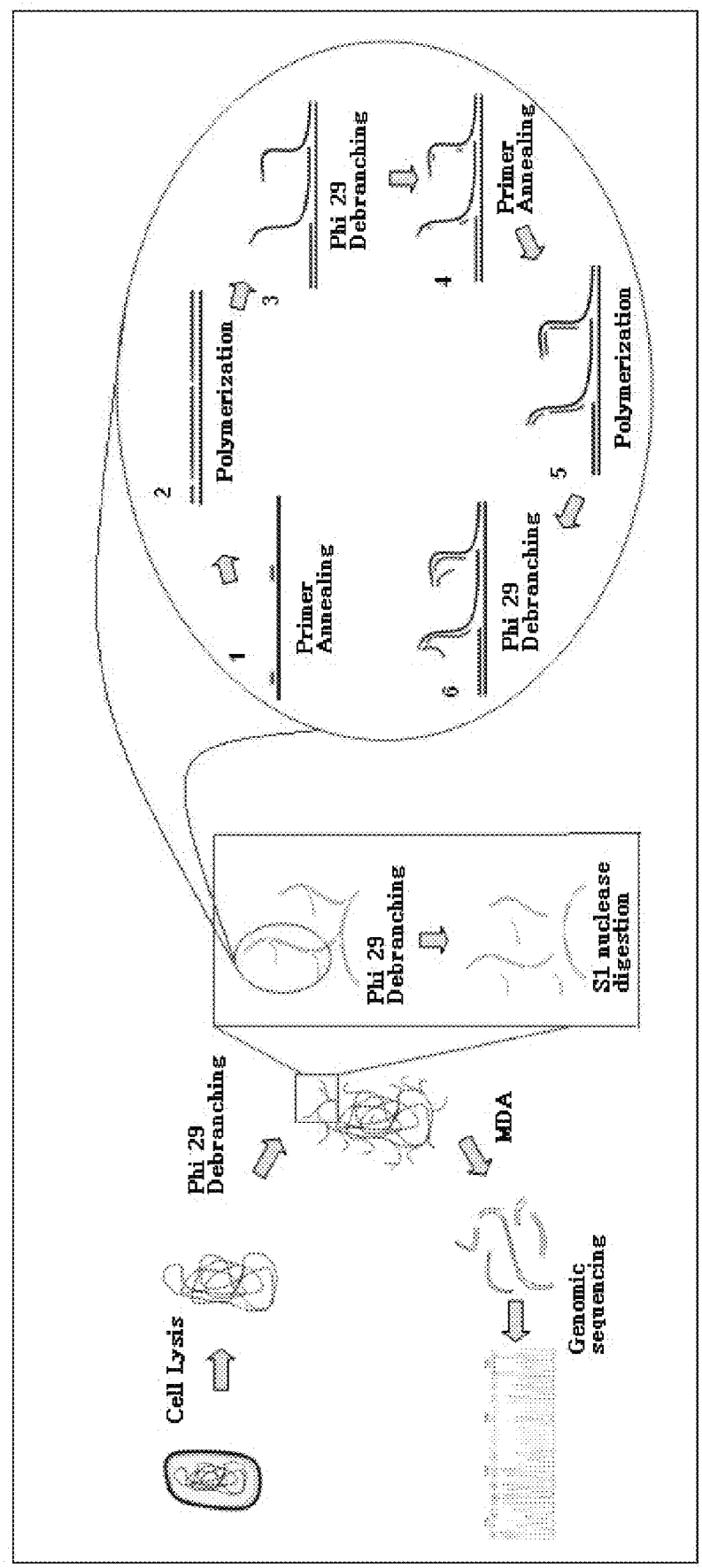
FIG. 1. Whole Genome Amplification (WGA).
Figure 2:
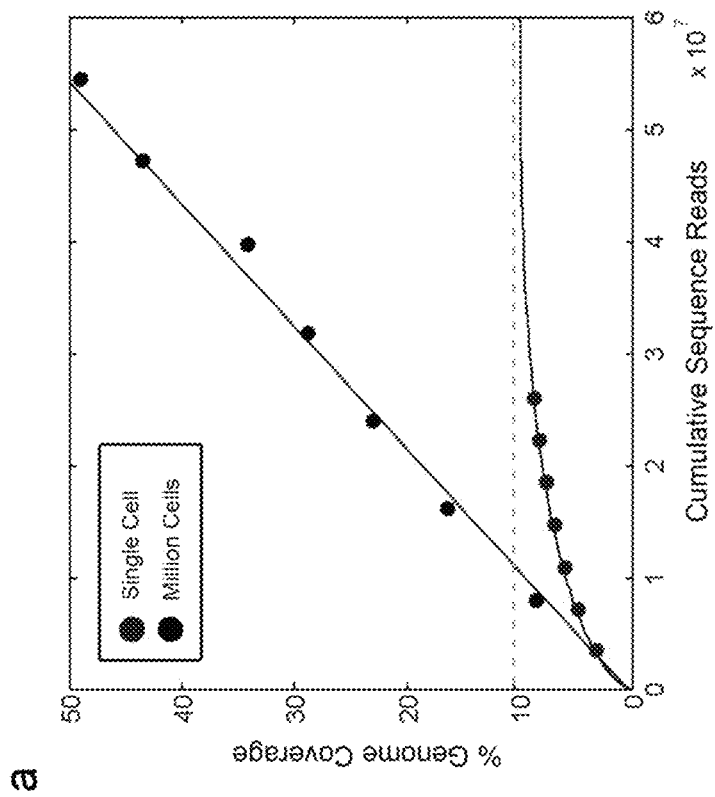
FIG. 2. Genome coverage comparison.
Figure 3:
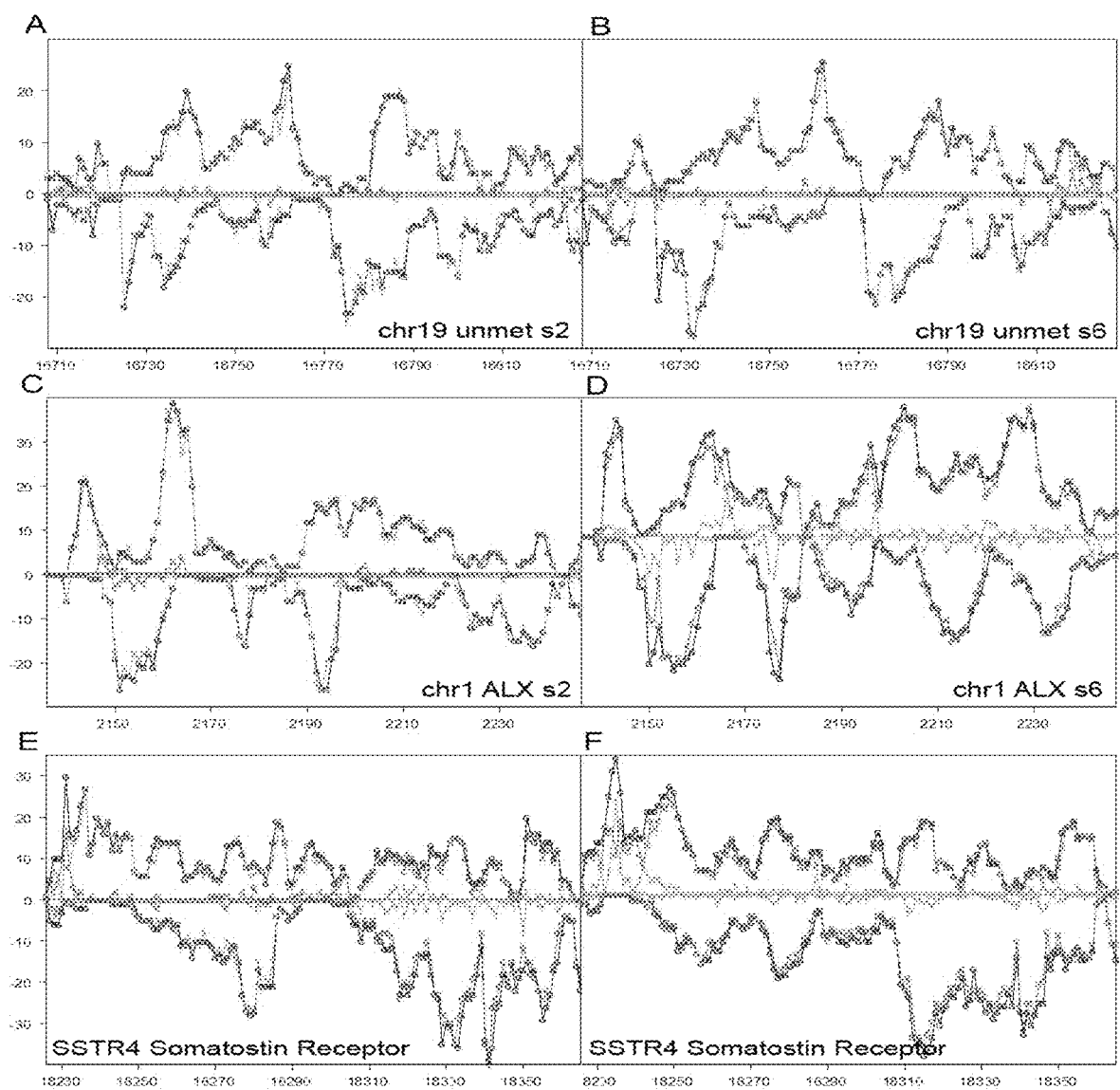

FIG. 3. Sequencing read counts for CpG dinucleotides within selected CpG islands Normal cell line SKN-1 (A,C,E) and breast cancer line MDA-MB-231 (B,D,F). Orange indicates I residues (unmethylated). Blue indicates C residues (methylated). Counts of the plus strand are above the X-axis, and counts on the minus strand are below.

Figure 4:
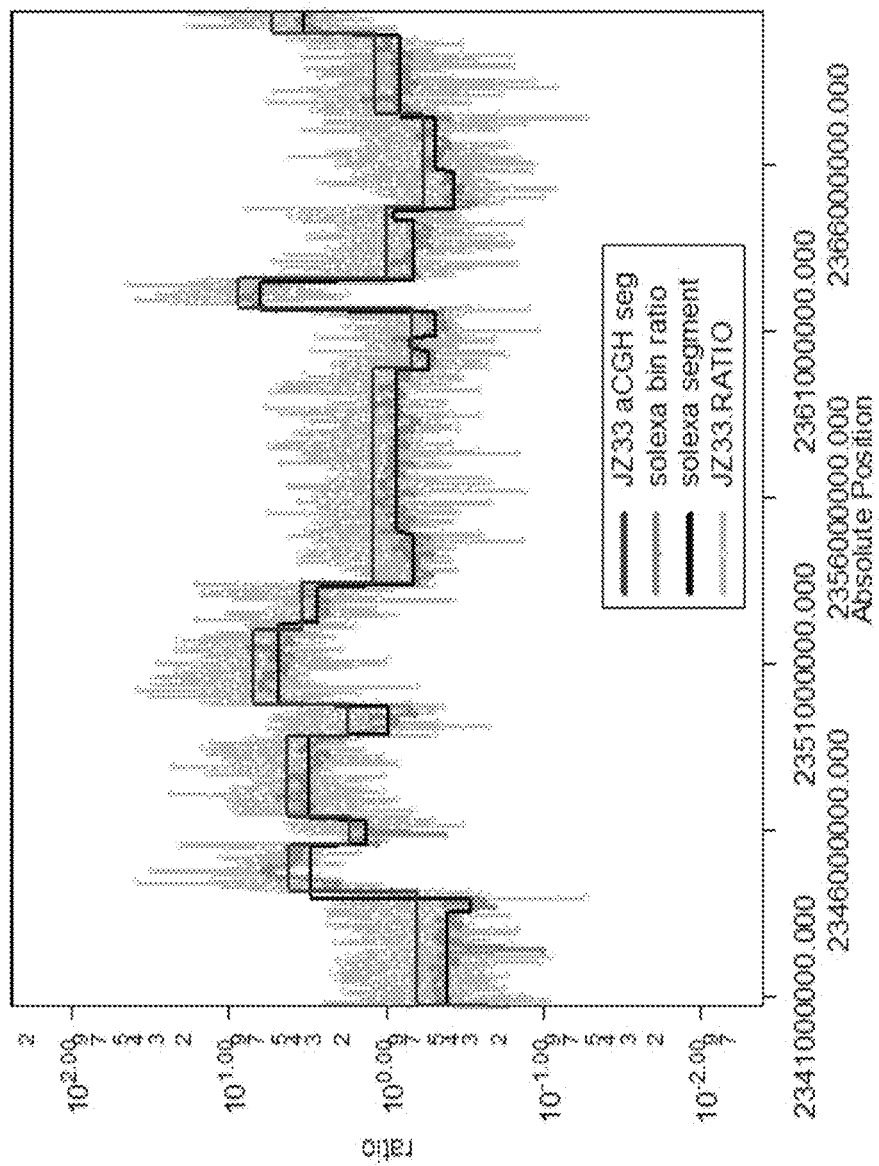

FIG. 4. Comparison of array CGH with 'sequence counting' for analyzing copy number data.

Graph shows a portion of chromosome 17 from FFPE sample JZ33 including raw (gray) ratio and segmented (green) data from array CGH, and raw sequence count data (orange) and its segmentation (blue).

Figure 5:
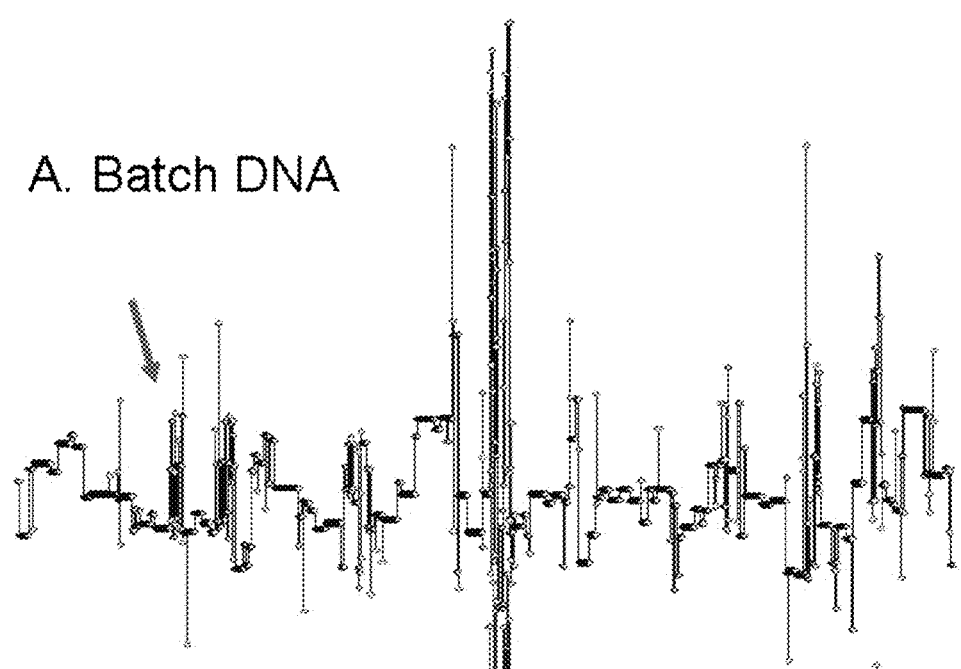
Figure 5:
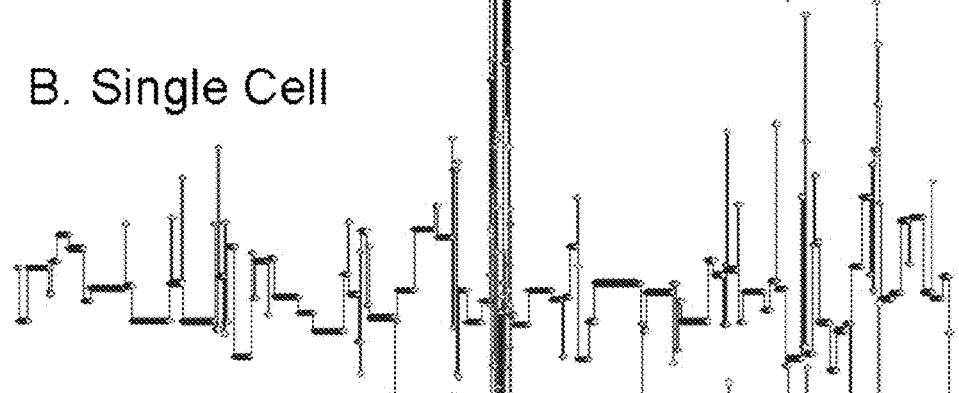
Figure 5:
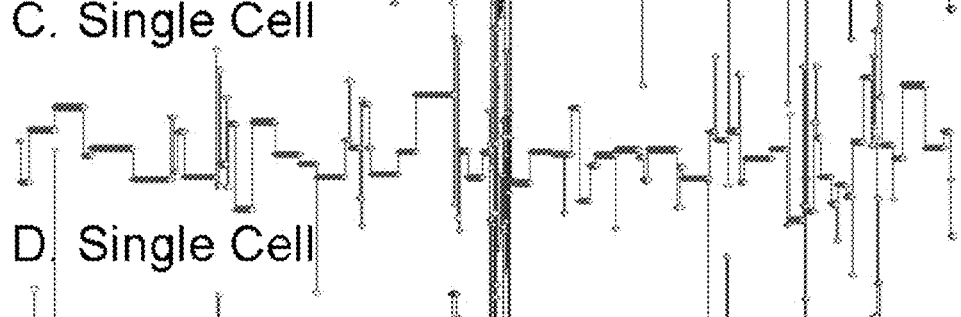
Figure 5:
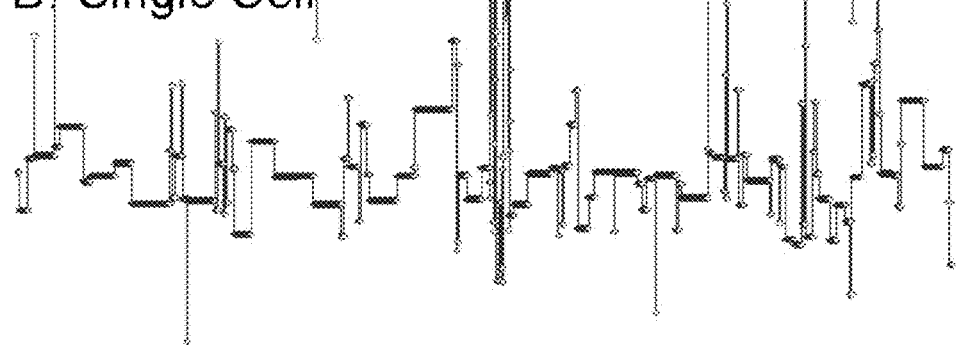

FIG. 5. ROMA CGH of sKBR3 compared with profiles of 3 independent single cell isolates derived from sparse DNA sequencing. (A) Batch DNA. (B, C, D) Single Cell.

Figure 6:
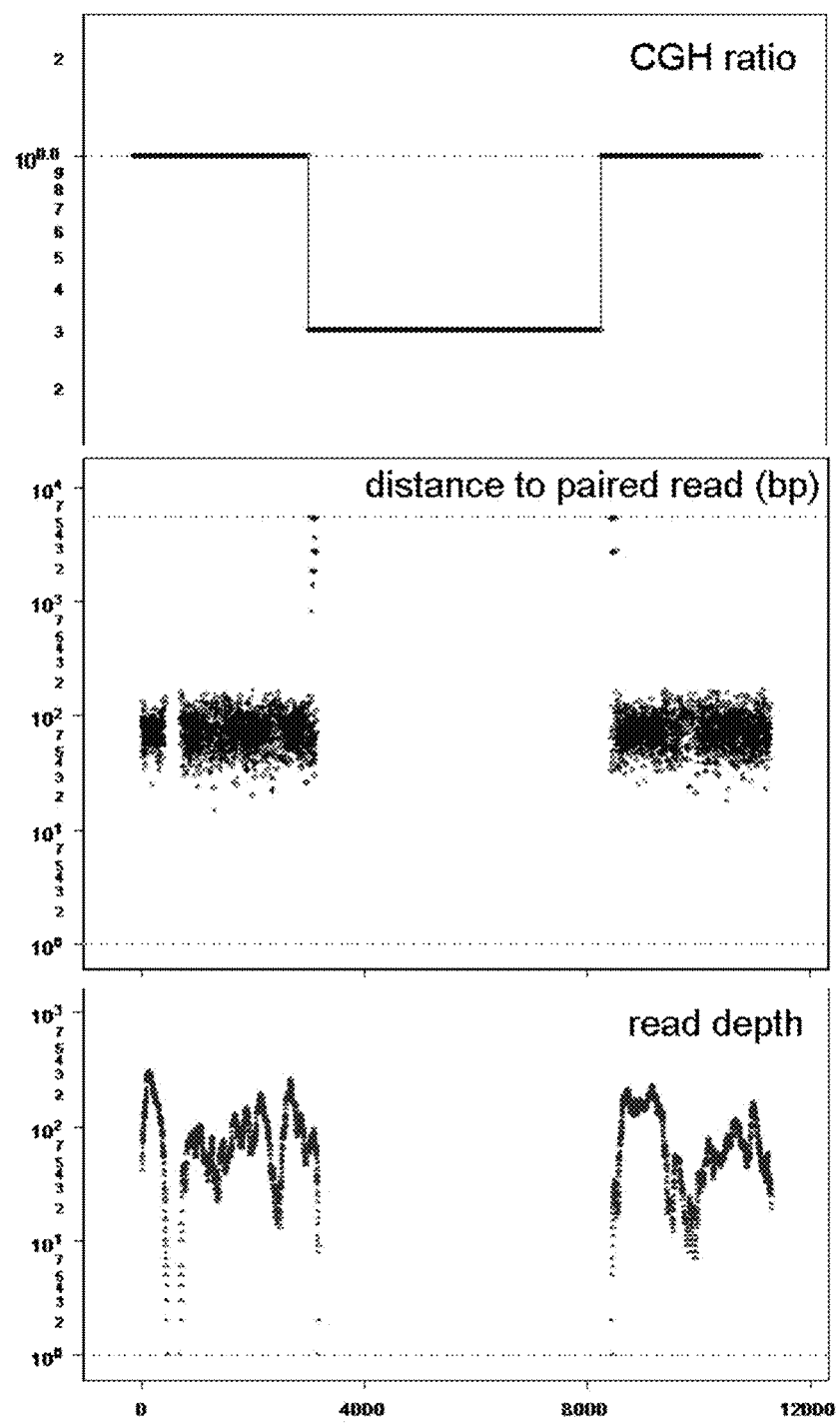

FIG. 6. Sequencing across the breakpoints of a homozygous deletion in cell on chromosome 5 line T47D.

Figure 7A:
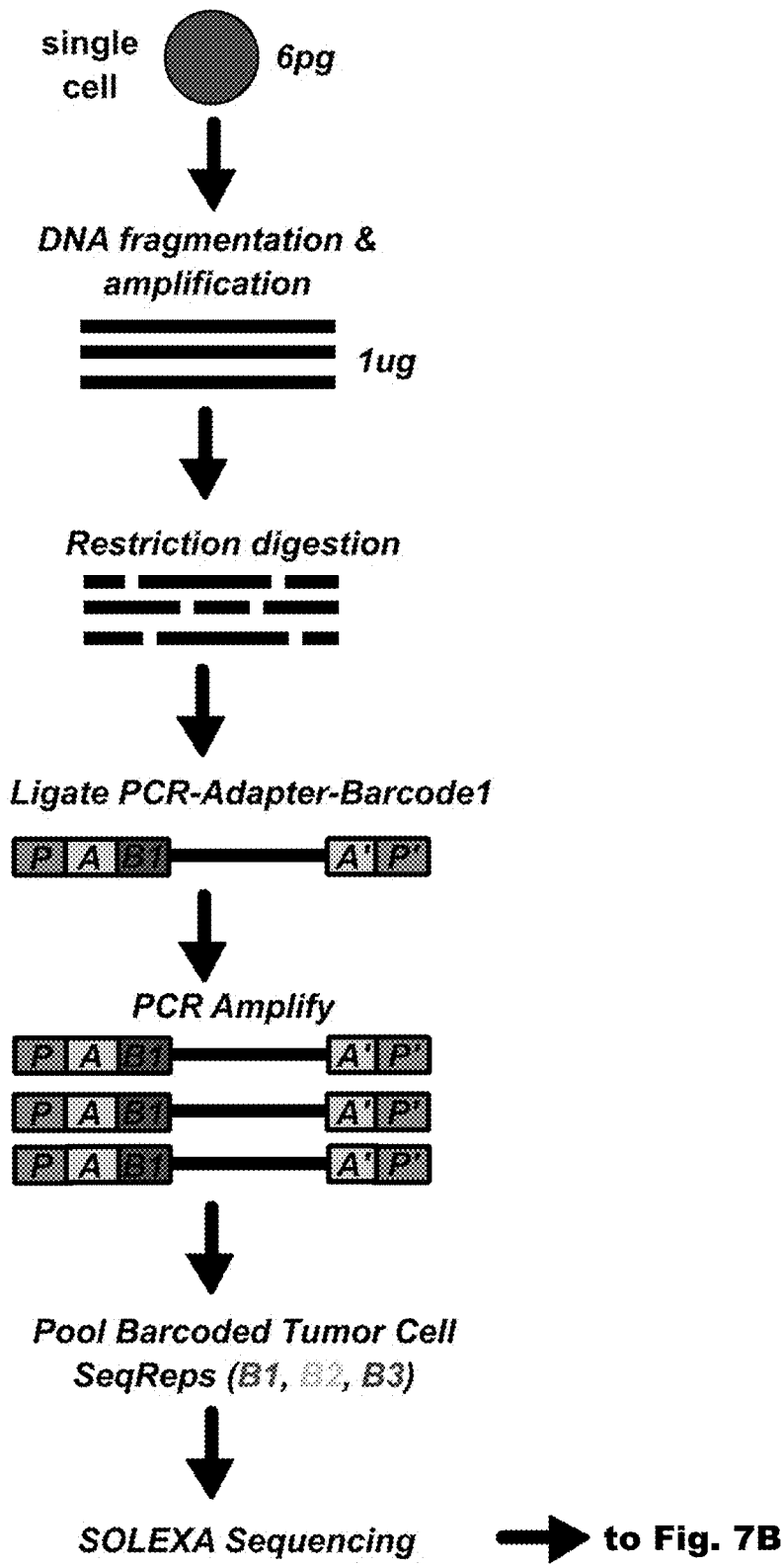

FIG. 7(A-C). Flowchart for genomic profiling by representational sequence counting FIG. 8. Scheme for varietal counting. Varietal tags are shown as random nucleotide sequences ($N_{10}$)

Flowchart of one embodiment of the invention.

Figure 9A:
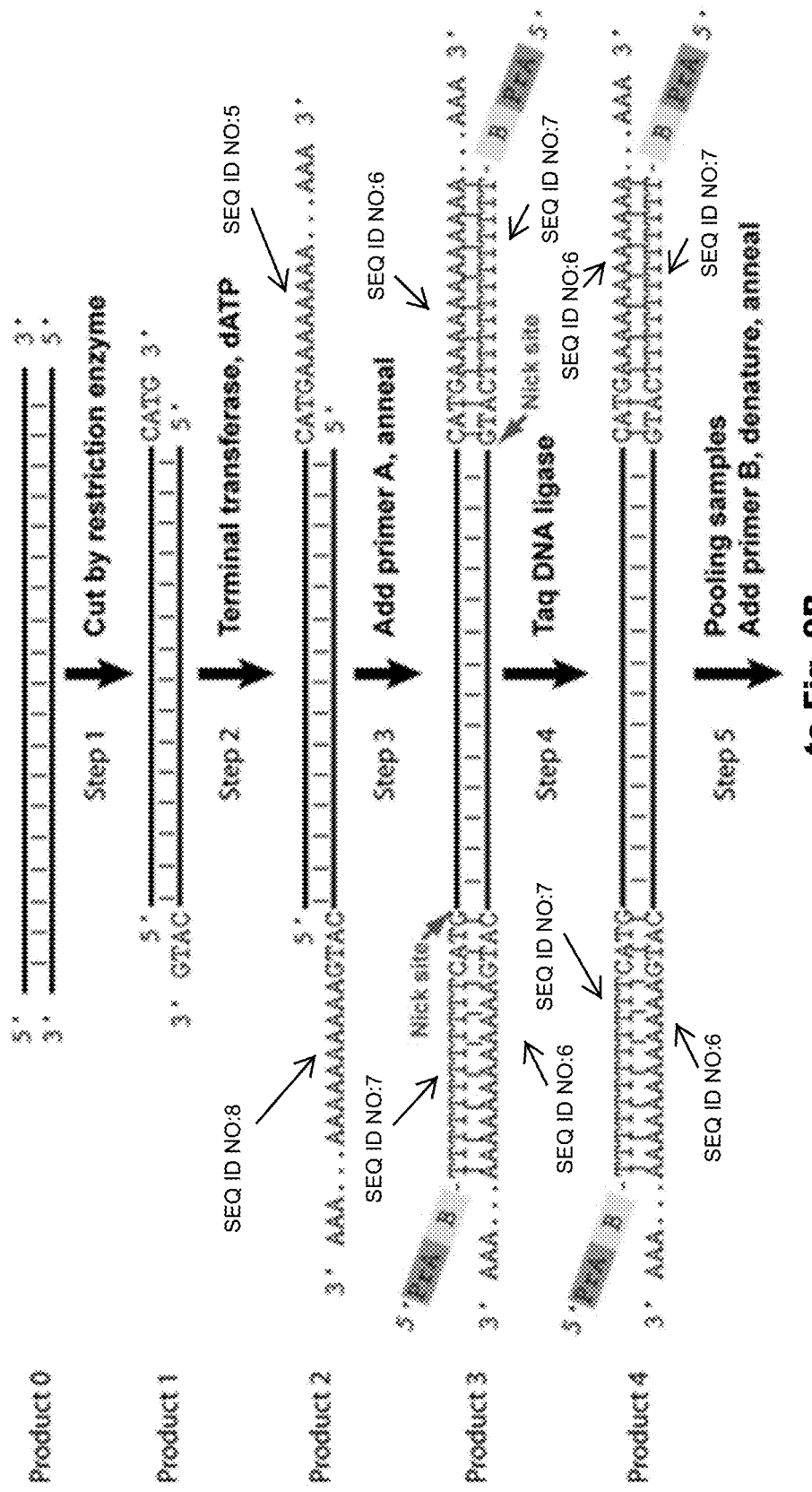

FIGS. 9(A and B). Nick ligation protocol

The sequence of primer A includes universal primer A (PrA; green), varietal tag (B; yellow), and oligo dT+CATG, the sequence of primer B includes universal primer B (PrB; orange) and oligo dT+CATG, PrA and PrB are universal primers, and cPrA (blue), cPrB (magenta), and cB (blue) are complementary to PrA, PrB and B, respectively.

Figure 10A:
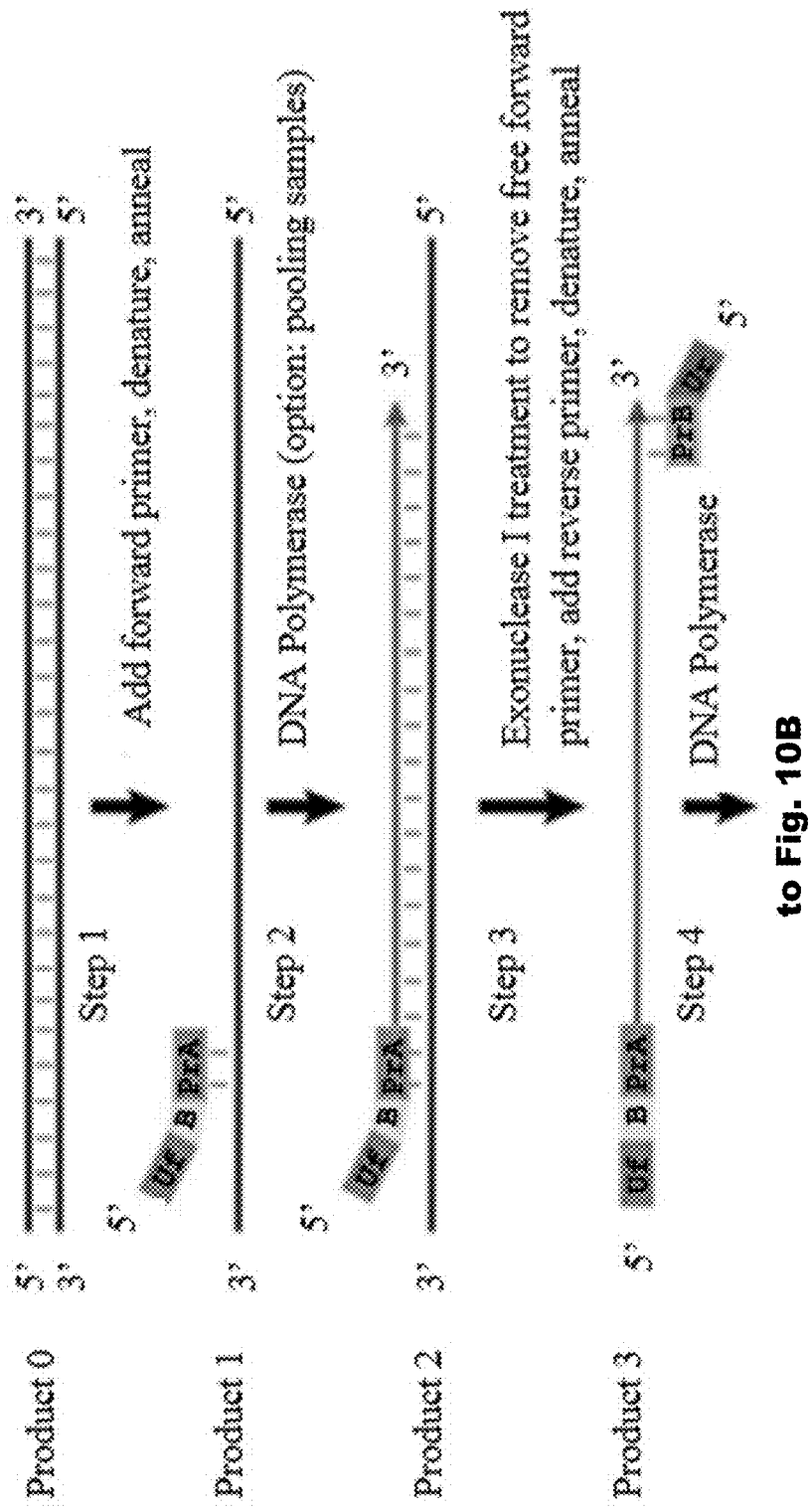

FIGS. 10(A and B). Schema for targeted sequencing of regional markers

UfBPrA is forward primer, B (yellow) is tag, UrPrR is reverse primer, PrB (brown) is gene-specific reverse primer, Uf (orange) is universal forward primer, PrA (blue) is gene specific forward primer, Ur (magenta) is universal reverse primer.

Figure 11:
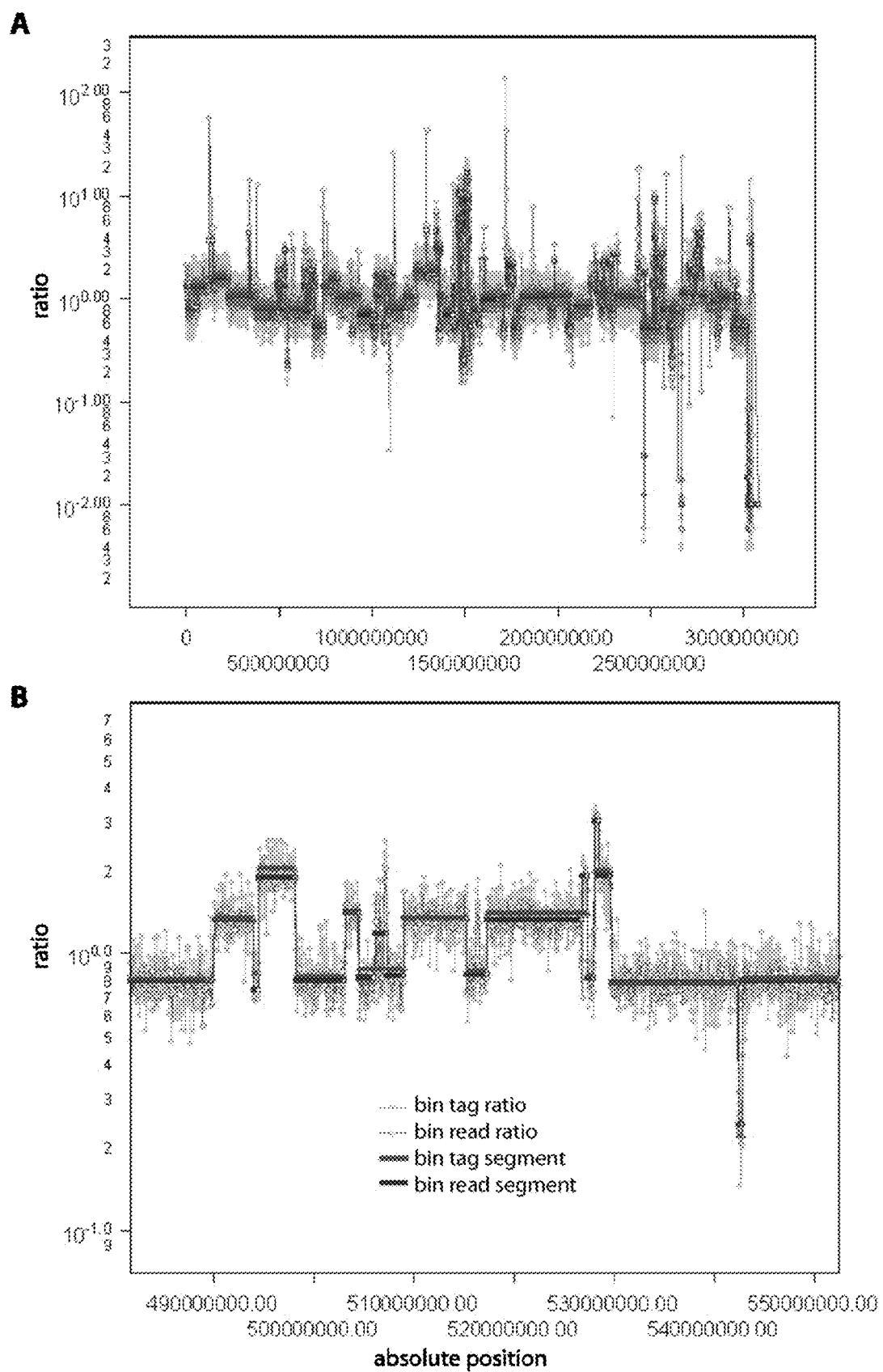

FIG. 11. Comparison of Varietal Counting with Sequence Counting

FIG. 11A shows genome wide copy number data. FIG. 11B shows partial genome copy number data.

DETAILED DESCRIPTION OF THE INVENTION

A method is provided for obtaining from genomic material genomic copy number information unaffected by amplification distortion, comprising:
a) obtaining segments of the genomic material;
b) tagging the segments with substantially unique tags to generate tagged nucleic acid molecules, such that each tagged nucleic acid molecule comprises one segment of the genomic material from step (a) and a tag;
c) subjecting the tagged nucleic acid molecules to amplification by polymerase chain reaction (PCR);
d) generating tag associated sequence reads sequencing the product of step (c);
e) assigning each tagged nucleic acid molecule to a location on a genome associated with the genomic material by mapping the subsequence of each tag associated sequence read corresponding to a segment of the genomic material to a location on the genome; and
f) counting the number of tagged nucleic acid molecules having a different tag that have been assigned to the same location on the genome,
thereby obtaining genomic copy number information unaffected by amplification distortion.

In an embodiment, the method further comprises estimating a genomic copy number of a region of the genome comprising more than one location on the genome by assigning as the copy number of the region the highest count obtained in step (f) for the locations within the region.

In an embodiment, the method further comprises comparing a count obtained in step (f) for a location on the genome to a count for the same location obtained from a reference sample, thereby estimating a relative genomic copy number of the location.

In an embodiment, the method further comprises
a) summing the counts obtained in step (f) for locations on the genome which comprise a first region of the genome, wherein the first region comprises more than one location;
b) summing the counts obtained in step (f) for locations on the genome which comprise a second region of the genome, wherein the second region is comprised of a number of locations which is comparable to the number of locations of the first region;
c) comparing the value obtained in step (a) to the value obtained in step (b),
thereby estimating the relative genomic copy number of the first region of the genome to the genomic copy number of the second region of the genome.

Step (b) of the above embodiment may further comprise
i) summing the counts obtained in step (f) for locations on the genome which comprise a third region of the genome, wherein the third region is comprised of a number of locations which is comparable to the number of locations of the first region; and
ii) obtaining an average of the sum of the counts obtained in step (f) for locations which comprise the second region and the sum of the counts obtained in step (f) for locations which comprise the third region.

In an embodiment of the method, the second region of the genome comprises a centromere.

In an embodiment, the method further comprises summing the counts obtained in step (f) for locations which comprise a region of the genome, and comparing the sum to a sum obtained from a reference sample for the same region of the genome, thereby estimating a relative genomic copy number of the region of the genome.

Also provided is a method for obtaining from mRNA transcripts mRNA copy number information unaffected by amplification distortion, comprising:
a) obtaining cDNA from the mRNA transcripts;
b) optionally obtaining segments of the cDNA;
c) tagging the cDNA or segments of cDNA with substantially unique tags to generate tagged nucleic acid molecules, such that each tagged nucleic acid molecule comprises
 i) one cDNA from step (a) or one segment of the cDNA from step (b), and
 ii) a tag;
d) subjecting the tagged nucleic acid molecules to amplification by polymerase chain reaction (PCR);
e) generating tag associated sequence reads by sequencing the product of step (d);
f) assigning each tagged nucleic acid molecule to a location on a cDNA library associated with the mRNA transcripts by mapping the subsequence of each tag associated sequence read corresponding to a cDNA or a segment of cDNA to a location on the cDNA library; and
g) counting the number of tagged nucleic acid molecules having a different tag that have been assigned to the same location on the cDNA library,
thereby obtaining mRNA copy number information unaffected by amplification distortion.

Also provided is a method for obtaining from mRNA transcripts mRNA copy number information unaffected by amplification distortion, comprising:
a) generating tagged nucleic acid molecules, comprising:
 i) subjecting the mRNA transcripts to a polymerase reaction in the presence of primers capable of hybridizing to the polyA tail of the mRNA transcripts under conditions that promote the formation of only one complement, thereby generating first order derivative strands;
 ii) adding a polynucleotide tail to the first order derivative strands; and
 iii) subjecting the first order derivative strands to a polymerase reaction in the presence of primers capable of hybridizing to the polynucleotide tail added in step (ii) under conditions that promote the formation of only one complement, thereby generating second order derivative strands,
wherein the primers of at least one of steps (i) and (iii) comprise substantially unique primers, thereby generating tagged nucleic acid molecules;
a) subjecting the tagged nucleic acid molecules to polymerase chain reaction (PCR) amplification;
b) generating tag associated sequence reads sequencing the product of step (b);
c) assigning each tagged nucleic acid molecule to a location on a cDNA library associated with the mRNA transcripts by mapping the subsequence of each tag associated sequence read corresponding to a mRNA transcript to a location on the cDNA library; and
d) counting the number of tagged nucleic acid molecules having a different tag that have been assigned to the same location on the cDNA library,
thereby obtaining mRNA copy number information unaffected by amplification distortion.

Also provided is a method for obtaining from genomic material DNA methylation information unaffected by amplification distortion, comprising:
a) obtaining segments of the genomic material;
b) adding a polynucleotide tail to the ends of the segments of the genomic material to generate zero-th order derivative strands;
c) subjecting the zero-th order derivative strands to a polymerase reaction in the presence essentially unique primers, wherein the essentially unique primers are capable of hybridizing to the polynucleotide tail of the zero-th order strands, under conditions that promote the formation of only one complement, thereby generating tagged nucleic acid molecules;
d) separating the tagged nucleic acid molecules into a group consisting of hemi-methylated tagged nucleic acid molecules and a group consisting of unmethylated tagged nucleic acid molecules;
e) subjecting each group of step (d) to amplification by polymerase chain reaction (PCR);
f) generating tag associated sequence reads by sequencing the product of step (e);
g) assigning each tagged nucleic acid molecule to a location on a genome associated with the genomic material by mapping the subsequence of to a segment of the genomic material to a location on the genome; and h) counting the number of tagged nucleic acid molecules having a different tag that have been assigned to the same location on the genome,
thereby obtaining DNA methylation information unaffected by amplification distortion.

In an embodiment of the methods, tagging the segments to generate tagged nucleic acid molecules comprises:
  a) adding a polynucleotide tail to the ends of the segments of the genomic material to generate zero-th order derivative strands;
  b) subjecting the zero-th order derivative strands of step (a) to a polymerase reaction in the presence of primers capable of hybridizing to the polynucleotide tail of the zero-th order strands under conditions that promote the formation of only one complement, thereby generating first order derivative strands;
  c) adding a polynucleotide tail to the first order derivative strands;
  d) subjecting the first order derivative strands to a polymerase reaction in the presence of primers capable of hybridizing to the polynucleotide tail of the first order derivative strands under conditions that promote the formation of only one complement, thereby generating second order derivative
  wherein the primers of at least one of steps (b) and (d) comprise substantially unique primers, thereby generating tagged nucleic acid molecules.

In an embodiment of the methods, tagging the segments to generate tagged nucleic acid molecules comprises
  a) adding a polynucleotide tail to the ends of the segments of genomic material to generate zero-tri order derivative strands,
  b) subjecting the zeroth order derivative strands of step (a) to a ligation reaction in the presence of primers capable of hybridizing to the polynucleotide tail of the zeroth order strands added in step (a) under conditions that promote the ligation of a primer to the 5' ends of the zeroth order derivative strands,
  c) subjecting the product of step (b) to a polymerase reaction in the presence of primers capable of hybridizing to the polynucleotide tail added in step (a) under conditions which promote the formation of only one complement, wherein the primers of step (c) have different nucleotide sequences than the primers of step (b), and wherein the polymerase has 3'-5' proofreading activity,
  wherein the primers of at least one of steps (b) and (c) comprise substantially unique primers, thereby generating tagged nucleic acid molecules.

In an embodiment of the methods, adding a polynucleotide tail comprises the use of a terminal transferase.

In an embodiment of the methods, tagging the segments to generate tagged nucleic acid molecules comprises ligation of adaptors comprising the tags to at least one end of the segments of the genomic material.

In an embodiment of the methods, the adaptors comprising the tags are ligated to only one end of the segments of the genomic material.

In an embodiment of the methods, the tags comprise a sequence that aids PCR amplification.

In an embodiment of the methods, each tagged nucleic acid molecule comprises one tag.

In an embodiment of the methods, each tagged nucleic acid molecule comprises more than one tag.

In an embodiment of the methods, segments of the genomic material are produced by restriction endonuclease digestion, mechanical shearing, heating, or sonication.

In an embodiment of the methods, segments of the cDNA are produced by restriction endonuclease digestion, mechanical shearing, heating, or sonication.

In an embodiment of the methods, the maximum copy number of a location on a cDNA library is not less than the number of tagged nucleic acid molecules having a different tag that have been assigned to the same location on the cDNA library.

An embodiment of the above methods further comprises analyzing mRNA copy number.

In an embodiment of the methods, separating the tagged nucleic acid molecules into a group consisting of hemimethylated tagged nucleic acid molecules and a group consisting of unmethylated tagged nucleic acid molecules is by cleavage with methylation sensitive restriction enzymes, partitioning with antibodies, or partitioning with methyl-C binding proteins directed to methylated or hydroxymethylated cytosine.

In an embodiment of the methods, the tagged nucleic acid molecules are subject to hybrid capture prior to PCR or prior to sequencing.

In an embodiment of the methods, each tagged nucleic acid molecule differs at more than one nucleotide.

In an embodiment of the methods, the tag sequences further comprise a sample tag.

In an embodiment of the methods, the tagged nucleic acid molecules are pooled with a plurality of tagged nucleic acid molecules having a different sample tag prior to amplification or prior to sequencing.

An embodiment of the methods further comprises deconvoluting the tag associated sequence reads by grouping the tag associated sequence reads according to sample tag.

In an embodiment of the methods, the tagged nucleic acid molecules are generated from a single species.

In an embodiment of the methods, the tagged nucleic acid molecules are generated from a single organism.

In an embodiment of the methods, tagged nucleic acid molecules are generated from a single cell.

In an embodiment, the single cell is from a needle aspirate of suspected cancer lesions.

In an embodiment, the single cell is from a core biopsy of suspected cancer lesions.

In an embodiment of the methods, the tagged nucleic acid molecules are generated from two or more organisms.

In an embodiment, the tagged nucleic acid molecules are generated from a single cell of each organism.

In an embodiment of the methods, the single species is human.

In an embodiment of the methods, the tagged nucleic acid molecules are generated from two or more species.

In an embodiment, the tagged nucleic acid molecules are generated from a population of microbes.

A further embodiment comprises comparing the genomic copy number information obtained for different species of the population to determine the relative count of those different species in the population.

Also provided is a composition of matter derived from genomic material comprising tagged nucleic acid molecules, said tagged nucleic acid molecules being produced by a process comprising:
  a) obtaining segments of the genomic material;
  b) adding a polynucleotide tail to the ends of the segments of the genomic material to generate zero-th order derivative strands;
  c) subjecting the zero-th order derivative strands of step (b) to a polymerase reaction in the presence of primers capable of hybridizing to the polynucleotide tail of the zero-th order strands under conditions that promote the formation of only one complement, thereby generating first order derivative strands;

d) adding a polynucleotide tail to the first order derivative strands;

e) subjecting the first order derivative strands to a polymerase reaction in the presence of primers capable of hybridizing to the polynucleotide tail of the first order derivative strands under conditions that promote the formation of only one complement, thereby generating second order derivative strands, wherein the primers of at least one of steps (c) and (e) comprise substantially unique primers, thereby generating tagged nucleic acid molecules.

Also provided is a composition of matter derived from genomic material comprising tagged nucleic acid molecules, said tagged nucleic acid molecules being produced by a process comprising:

a) obtaining segments of genomic material;

b) adding a polynucleotide tail to the ends of the segments of genomic material to generate zero-th order derivative strands, c) subjecting the zero-th order derivative strands of step (b) to a ligation reaction in the presence of primers capable of hybridizing to the polynucleotide tail of the zero-th order strands added in step (b) under conditions that promote the ligation of a primer to the 5' ends of the zero-th order derivative strands, d) subjecting the product of step (c) to a polymerase reaction in the presence of primers capable of hybridizing to the polynucleotide tail added in step (b) under conditions which promote the formation of only one complement, wherein the primers of step (d) have different nucleotide sequences than the primers of step (c), and wherein the polymerase has 3'-5' proofreading activity, wherein the primers of at least one of steps (c) and (d) comprise substantially unique primers, thereby generating tagged nucleic acid molecules.

Also provided is a composition of matter derived from a mRNA transcripts comprising tagged nucleic acid molecules, said tagged nucleic acid molecules being produced by a process comprising:

a) obtaining cDNA from the mRNA transcripts;

b) optionally obtaining segments of the cDNA; and c) tagging the cDNA or segments of cDNA with substantially unique tags to generate tagged nucleic acid molecules, wherein each tagged nucleic acid molecule comprises
  i) one cDNA from step (a) or one segment of the cDNA from step (b) and
  ii) a tag.

Also provided is a composition of matter derived from mRNA transcripts comprising tagged nucleic acid molecules, said tagged nucleic acid molecules being produced by a process comprising:

a) obtaining mRNA transcripts;

b) subjecting the mRNA transcripts to a polymerase reaction in the presence of primers capable of hybridizing to the polyA tail of the mRNA transcripts under conditions that promote the formation of only one complement, thereby generating first order derivative strands;

c) adding a polynucleotide tail to the first order derivative strands;

d) subjecting the first order derivative strands to a polymerase reaction in the presence of primers capable of hybridizing to the polynucleotide tail added in step (c) under conditions that promote the formation of only one complement, thereby generating second order derivative strands, wherein the primers of at least one of steps (b) and d) comprise substantially unique primers, thereby generating tagged nucleic acid molecules.

In an embodiment of the above compositions, adding a polynucleotide tail comprises the use of a terminal transferase.

In an embodiment of the above compositions, each tagged nucleic acid molecule comprises one tag.

In an embodiment of the above compositions, each tagged nucleic acid molecule comprises more than one tag.

In an embodiment of the above compositions, segments of the genomic material are produced by restriction endonuclease digestion, mechanical shearing, heating, or sonication.

In an embodiment of the above compositions, segments of the cDNA are produced by restriction endonuclease digestion, mechanical shearing, heating, or sonication.

In an embodiment of the above compositions, the complexity of the tagged nucleic acid molecules is reduced by hybrid capture.

In an embodiment of the above compositions, each tagged nucleic acid molecules differs at more than one nucleotide.

In an embodiment of the above compositions, the tag sequences further comprise a sample tag.

Also provided is a composition of matter comprising at least two pools of tagged nucleic acid molecules as described herein.

In an embodiment of the above compositions, the tagged nucleic acid molecules are generated from a single cell.

In an embodiment, the single cell is from a needle aspirate of suspected cancer lesions.

In an embodiment, the single cell is from a core biopsy of suspected cancer legions.

In an embodiment of the above compositions, the tagged nucleic acid molecules are generated from two or more organisms.

Also provided is a kit for determining nucleic acid copy number information unaffected by amplification distortion comprising:

a) a terminal transferase, and b) plurality of substantially unique primers,
  wherein the substantially unique primers comprise substantially unique tags, and wherein the substantially unique primers are capable of hybridizing to the polynucleotide tail of a nucleic acid molecule which has a polynucleotide tail added by the terminal transferase.

In an embodiment, the kit further comprises a DNA polymerase having 3'-5' proofreading activity.

In an embodiment of the kits, the plurality of substantially unique primers comprises $10^n$ primers, wherein n is an integer from 2 to 9.

In an embodiment, the kits further comprise a second terminal transferase and a primer capable of hybridizing to the polynucleotide tail of a nucleic acid molecule which has a polynucleotide tail added by the second terminal transferase.

In an embodiment of the kits, the tags are six nucleotides long.

In an embodiment of the kits, the tags are 15 nucleotides long.

In an embodiment, the kits further comprise sample tags.

In an embodiment, the sample tags are 2 nucleotides long.

In an embodiment, the sample tags are 4 nucleotides long.

In an embodiment, the sample tags comprise a sample tag set.

In an embodiment of the above kits, the substantially unique tags comprise the sample tags.

Terms

For the purpose of this invention, different words and phrases are defined as follows:

As used herein, the term "adaptor" refers to an oligonucleotide or nucleic acid fragment or segment that can be ligated to a nucleic acid molecule of interest. For the purposes of this invention adaptors may, as options, comprise primer binding sites, recognition sites for endonucleases, common sequences, promoters, tag sequences, and sample tag sequences. Preferably, adaptors are positioned to be located on both sides (flanking) a particular nucleic acid molecule of interest. In accordance with the invention, adaptors may be added to nucleic acid molecules of interest by standard recombinant techniques (e.g. restriction digest and ligation). For example, adaptors may be added to a population of linear molecules, (e.g. a genomic DNA which has been cleaved or digested) to form a population of linear molecules containing adaptors at one and preferably both termini of all or a substantial portion of molecules. The adaptor may be entirely or substantially double stranded or entirely single stranded. A double stranded adaptor may comprise two oligonucleotides that are at least partially complementary. The adaptor may be phosphorylated or unphosphorylated on one or both strands. Adaptors may be used for DNA sequencing. Adaptors may also incorporate modified nucleotides that modify the properties of the adaptor sequence. For example, methylated cytosines may be substituted for cytosines. In an embodiment of this invention the adaptors ligated to genomic DNA to enable cluster generation on the sequencer contain cytosines which were all methylated. This modification protects such adaptors from bisulfite conversion, and is taken into account in the downstream applications and analysis of this invention.

As used herein, the term "amplifying" refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., polymerase chain reaction (PCR)) such that the amount of amplification product increasing, often times exponentially, although exponential amplification not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

As used herein, the term "amplification distortion" refers to non-uniform amplification of template nucleic acid molecules.

As used herein, the term "bisulfate-treatment" refers to the treatment of nucleic acid with a reagent used for the bisulfite conversion of cytosine to uracil. Examples of bisulfite conversion reagents include but are not limited to treatment with a bisulfite, a disulfate or a hydrogensulfite compound.

As used herein, the term "bisulfite-converted material" refers to a nucleic acid that has been contacted with bisulfite ion in an amount appropriate for bisulfite conversion protocols known in the art. Thus, the term "bisulfite-converted material" includes nucleic acids that have been contacted with, for example, magnesium bisulfite or sodium bisulfite, prior to treatment with base.

As used herein, the term "sequence capture" or "hybrid capture" refers to a process of hybridizing a "capture probe" to a nucleic acid having a sequence which is complementary to the sequence of the capture probe. A capture probe may be immobilized to a substrate on a solid phase microarray, wherein "substrate" refers to short nucleic acid sequences which are known. Their location on the solid phase microarray may or may not be predetermined. The capture probe comprising a "sequence complementary to the substrate" may be immobilized to the solid phase microarray by hybridizing to its complementary "substrate sequence."

As used herein, the term "clamp" refers to a nucleotide sequence of CC, CG, GC or GG which may be located at the first two nucleotide positions at the 5' end of a primer, tag, or sample tag, or the last two nucleotide positions at the 3' end of a primer, tag, or sample tag.

As used herein, the term "comparable number of locations" means that a first genomic region has a number of locations on the genome which is within 25% of the number of locations of a second genomic region. In an embodiment, the first genomic region which has a comparable number of locations to the second genomic region has a number of locations which is within 20%, 15%, 10%, 5%, 1%, or exactly the same as the number of locations of the second genomic location.

As used herein, a subsequence of a tag associated sequence read is "corresponding to" a tag when the subsequence is identical to the nucleotide sequence of the tag.

As used herein, a subsequence of a tag associated sequence read is "corresponding to" a species of a nucleic acid molecule when the subsequence is substantially identical to or substantially complementary to at least about 10, 12, 14, 16, 18, 20, or more nucleotides of the sequence of the species of nucleic acid molecule. In an embodiment, the subsequence is identical to or fully complementary to at least about 10, 12, 14, 16, 18, 20, or more nucleotides of the sequence of the species of nucleic acid molecule.

The term "CpG site" refers to the CpG dinucleotide.

As used here, the term "CpG island" refers to a region of DNA with a high G+C; content and a high frequency of CpG dinucleotides relative to the bulk genome, as further defined at the UCSC Genome Bioinformatics Site at genme.ucsc.edu/
index.html?org=Human&db=hg19&hgsid=171216665, and in particular, by annotation in the USCS Genome Bioinformatics Site database ((CpG Islands Track or Table: cpgIslandExt).

As used herein, the term "fully complementary" refers to the reverse complement of a nucleic acid sequence.

As used herein, the term "library" refers to a collection of nucleic acid molecules (circular or linear). In one preferred embodiment, a library representative of all of the DNA content of an organism (such a library is referred to as a "genomic" library), or a set of nucleic acid molecules representative of all of the expressed genes (such a library is referred to as a cDNA library) in a cell, tissue, organ or organism. A library may also comprise random sequences made by de novo synthesis, mutagenesis of one or more sequences and the like. A library may be contained in one vector.

As used herein, the term "mapping" refers to identifying a location on a genome or cDNA library that has a sequence which is substantially identical to or substantially fully complementary to the subsequence of a tag associated sequence read corresponding to a species of nucleic acid molecule, and assigning the tag associated sequence read or the tagged nucleic acid molecule generating the tag associated sequence read to the location. The nucleic acid molecule may be, but is not limited to the following: a segment of genomic material, a cDNA, a mRNA, or a segment of a cDNA.

As used herein, the term. "methylation" refers to the covalent attachment of a methyl group at the C5-position of the nucleotide base cytosine within the CpG dinucleotides of genomic region of interest. The term "methylation state" or refers to the presence or absence of 5-methyl-cytosine (5-Me") at one or a plurality of CpG dinucleotides within a DNA sequence. A methylation site is a sequence of contiguous linked nucleotides that is recognized and methylated by a sequence specific methylase. A methylase is an enzyme that methylates (i.e., covalently attaches a methyl group) one or more nucleotides at a methylation site.

As used herein, the term "mRNA transcript" refers to the nucleic acid molecule resulting from transcription of DNA.

As used herein, the term "pool" means to combine one plurality of nucleic acid molecules with at least one other plurality of nucleic acid molecules. In an embodiment, tagged nucleic acid molecules are pooled. Pooling may be done after any step in which tagged nucleic acid molecules are generated. In an embodiment, pooling is done prior to PCR and/or prior to sequencing. In an embodiment, tagged nucleic acid molecules generated from a single cell are pooled with tagged nucleic acid molecules generated from a different single cell.

As used herein, the term "probe array" refers to an array of N different nucleic acid molecules deposited on a reaction substrate which serve to interrogate mixtures of target molecules or multiple sites on a single target molecule administered to the surface of the array.

As used herein, the term "read" or "sequence read" refers to the nucleotide or base sequence information of a nucleic acid that has been generated by any sequencing method. A read therefore corresponds to the sequence information obtained from one strand of a nucleic acid fragment. For example, a DNA fragment where sequence has been generated from one strand in a single reaction will result in a single read. However, multiple reads for the same DNA strand can be generated where multiple copies of that DNA fragment exist in a sequencing project or where the strand has been sequenced multiple times. A read therefore corresponds to the purine or pyrimidine base calls or sequence determinations of a particular sequencing reaction.

As used herein, the term "reference genome" refers to a genome of the same species as that being analyzed for which genome the sequence information is known.

As used herein, the term "region of the genome" refers to a continuous genomic sequence comprising multiple discrete locations.

As used herein, the term "representation of DNA" or "representation of a genome" refers to a sampling of the DNA or genome produced by a restriction endonuclease digestion of genomic or other DNA, followed by linkage of adaptors and then amplification with primers complementary to the adaptors.

As used herein, the term "sample tag" refers to a nucleic acid having a sequence no greater than 1000 nucleotides and no less than two that may be covalently attached to each member of a plurality of tagged nucleic acid molecules or tagged reagent molecules. A "sample tag" may comprise part of a "tag."

As used herein, the term "sample tag set" refers to a plurality of unique sample tags of the same length, wherein the nucleotide sequence of each unique sample tag differs from the nucleotide sequence of any other unique sample tag in the sample tag set at two or more corresponding positions in the sequence. A unique sample tag selected from the sample tag set may be covalently attached to each member of a unique sample consisting of a plurality of tagged nucleic acid molecules in order to identify a tagged nucleic acid molecule as a member of that unique sample.

As used herein, the term "segments of cDNA," refers to the nucleic acid molecules resulting from fragmentation of cDNA.

As used herein, the term "segments of genomic material" refers to the nucleic acid molecules resulting from fragmentation of genomic DNA.

A nucleic acid molecule which contains a sequence of nucleotides identical to a segment, of a cDNA or a segment of genomic material comprises a "segment of cDNA" or a "segment of genomic material," respectively.

As used herein, the "sequence complexity" or "complexity" with regards to a population of polynucleotides refers to the number of different species of polynucleotides present in the population.

As used herein, "substantially identical" or "substantially fully complementary" sequences have at least about 80% sequence identity or complementarity, respectively, to a nucleotide sequence. Substantially identical sequences or substantially fully complementary sequences may have at least about 85%, 90%, 95% or 100% sequence identity or complementarity, respectively.

As used herein, the term "substantially unique primers" refers to a plurality of primers, wherein each primer comprises a tag, and wherein at least 50% of the tags of the plurality of primers are unique. Preferably, the tags are at least 60%, 70%, 80%, 90%, or 100% unique tags.

As used herein, the term "substantially unique tags" refers to tags in a plurality of tags, wherein at least 50% of the tags of the plurality are unique to the plurality of tags. Preferably, substantially unique tags will be at least 60%, 70%, 80%, 90%, or 100% unique tags.

As used herein, the term. "tag" refers to a nucleic acid having a sequence no greater than 1000 nucleotides and no less than two that may be covalently attached to a nucleic acid molecule or reagent molecule. A tag may comprise a part of an adaptor or a primer.

As used herein, a "tagged nucleic acid molecule" refers to a nucleic acid molecule which is covalently attached to a "tag."

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All combinations of the embodiments of the invention described herein are within the scope of the invention unless clearly indicated otherwise.

Single Cell Number Profiling by 'Sequence Counting' and Sample Tagging.

High throughput sequencers are in effect single molecule sequencers. Because the human genome is sequenced and assembled, a single molecule sequencer is also a single molecule identifier. Therefore, sequencing is also counting, as illustrated in FIG. 4 which illustrates how low coverage sequencing can yield an estimate of copy number which is comparable to array hybridization. The distinction for this is that 'sequence counting' can be done on single cells, and, using the multiplex system disclosed herein, relatively inexpensively, in effect converting the high throughput sequencer into a detector of single cells with abnormal genomes. To the sequencing technology two additional features were added: limiting dilution and sample tagging. For single-cell sequencing, the single cells or the nuclei of the single cells are first deposited into separate wells or are kept physically separated by other means, i.e. a gel. The single cells or the nuclei of cells can be deposited in a well by a cell sorter. Alternatively a collection of cells or nuclei can be diluted into a fluid that is then made semi-solid. A unique sample tag is prepared for each well for sequencing, with a separate sample tag per well. After this step, the wells are pooled and sequenced. The sample tag is used to deconvolute the information, allowing a copy number profile to be made for each individual cell.

Protocol: Isolate single tumor cells or single nuclei of the tumor cell, tag and optionally sample tag the DNA of each cell or nuclei, and amplify the tagged DNA to microgram quantities to generate tagged libraries for Solexa sequencing. The isolation of single tumor cells will occur by Fluorescent Activated Cell Sorting by total genomic DNA content, to deposit single nuclei into individual wells.

Alternatively, tumor cells can be isolated by FACS sorting with fluorescent antibodies against breast epithelium markers, including cytokeratin 8, 18 or 19. Cells are lysed in situ and the genome is fragmented by heating. Libraries are constructed from the fragmented genomic DNA. Preliminary experiments were conducted using high-resolution ROMA microarray to quantify whole-genome copy number on DNA amplified using WGA from single SK-BR-3 cells (FIG. 5). These experiments demonstrate the feasibility and efficiency of amplifying 6 pg of DNA into microgram quantities to determine copy number by microarray methods, which suggests that the DNA is also suitable for determining copy number by sequencing.

Since sequencing whole tumor genomes from single cells is costly and time consuming, two methods are proposed to stratify the genome and sequence for copy number: Representation Sequencing and Bin Sequencing.

Representation Sequencing

Representation sequencing involves restriction digesting genomic DNA into fragments and sequencing only the stratified population of restriction fragments to determine copy number. This method has the advantage of generating precise restriction fragments that can be reliably prepared as libraries from different individual tumor cells. In this protocol genomic DNA is amplified from a single tumor cell, digested with the DpnII, a second digestion is preformed with a AluI enzyme to remove highly repetitive "Alu SINE elements," sequencing adaptors (Illumina GA, Solexa) with a unique 4 nucleotide sample tag are ligated and the ligated fragments are PCR amplified to generate a sequencing library. In silico modeling predicts that the double digest will increase the fraction of unique sequencing reads to 75% from the 55% normally seen in unselected human genome sequencing. The sample tagged DNA libraries are then pooled, and applied to the Solexa flow-cells for cluster amplification and single read sequencing. Single-end reads are used because they are faster and cheaper than paired-end reads and provide ail of the information necessary for 'sequence counting'. Mapping algorithms then align each sequence read with a high quality score (with a read length in excess of 35 bp) and an unambiguous sample tag to a specific location on the DpnII restriction map of the human genome. The result is a count of reads at places in the genome, similar to the process demonstrated in FIG. 4, except that the data is segregated by sample tag, so that each well receives a copy number profile.

Bin Sequencing

It is clear that sequencing of random size-selected fragment from the genome is a viable alternative. In this method, the DNA from single tumor cells is amplified to generate fragments from 200-2000 bp. Blunt-end cloning is then used to ligate adaptors to these fragments, followed by PCR amplification to generate libraries (standard Solexa protocol for single read genomic DNA). However, in addition to this protocol adaptor sequences with 4 nucleotide sample tags are ligated to generate unique libraries from each tumor cell genome. The sample tagged DNA libraries are then pooled, and applied to the Solexa flow-cells for cluster amplification and single read sequencing. The 35 bp sequences are then mapped to specific regions of the human genome and deconvoluted using the unique sample tag to determine which sequence reads originated from which tumor cells. The crucial step in this procedure that is different from representation methods is to artificially divide the human genome into "bins" of several kilobases. Break analysis in sequence count data has another degree of freedom compared to what is practiced for array data, namely that the boundaries of the bins can be adjusted so as to minimize variance. Each bin contains a number of random genomic sequence reads from which a mean value is computed to determine genomic copy number at low sequence coverage.

The particular use of the WGA method does not depend on absolutely uniform amplification across the genome. Useful data can be obtained even if only half of the potential fragments from a single cell were amplified in a given reaction. Additionally, redundancy of data gained from segmentation benefits in identifying breakpoints.

Representation Sequencing vs. Bin Sequencing

A comparison of the two methods reveals the number of samples that can be profiled per sequencing run. Of the 3,149,324 Dpn II fragments in size range 200-800 (size optimal for sequencing) there are 618,629 not cut with AluI and thus available to be amplified. Approximately 5% of the fragment ends, or about 450,000, yield unique mappings and thus provide locations for counting. The overall process is presented as a flowchart in FIG. 7.

Assuming 15 million quality reads per Solexa sequencing lane, random sequencing yields about or 8.25 million unique reads per lane. The DpnII/AluI representation should increase the number of unique reads to 11.25 million. Modeling a single flow cell lane with 100 kb bins distributed across the genome, the projected results are as follows:

TABLE 1

| # samples | avg reads/bin/sample (random) | avg. reads/bin/sample (Dpn/Alu) |
|---|---|---|
| 1 sample per lane | 267 | 363 |
| 2 samples per lane | 133 | 181 |
| 12 samples per lane | 22 | 30 |

The number of samples (individual cells) to be sequenced per lane, is between 4 and ten. With 8 lanes on a flowcell, 30-80 samples could be profiled at the level of FIG. 4 relatively inexpensively.

Finally, the whole genomic copy number (generated by sequencing) will be determined for multiple, individual tumor cells in a single solid tumor. The data will be segmented into sections that minimize variance of copy number, subject to Kolmogorov-Smirnov significance tests, to generate individual tumor copy number profiles. As stated above, an additional degree of freedom, which our algorithms do not yet incorporate, is selecting the "boundary" of the bins. The single cell tumor genome profiles will be compared to study tumor heterogeneity in single solid tumors which may elucidate the progression of genomic events during tumorigenesis.

Varietal Counting of Nucleic Acids

Measuring the absolute or relative concentration of nucleic acid sequences in a sample often suffers from severe stochastic distortions due to differential amplifications or losses during processing and manipulation of the nucleic acids. There is never more information available than the number of molecules of the starting material in the sample itself. The method described herein is designed to capture the information at the earliest stage, in a form that is then resistant to distortion by further amplification.

Input nucleic acid molecules (0-th order derivatives), or first round copies of them (1-st order derivatives), present in the sample, can be randomly tagged using a large choice of distinct tags. Every tagged molecule becomes essentially unique, the combination of the information in the tag and the information in the nucleic acid, which can later be read by sequencing. The combination of a tag with a 0-th order, 1-st order, or subsequent N-th order nucleic acid molecule is called a "tagged nucleic acid molecule." After amplification or selection or other processing, the number of different tags is counted.

Within a pool of tagged nucleic acid molecules, each tagged nucleic acid molecule is likely unique in the pool when a sufficiently large number of distinct tags is used. Then in subsequent amplifications these unique tagged nucleic acid molecules are amplified to facilitate detection, but no new species of tagged nucleic acid molecules are created. Thus, distorted counts are not created provided that the number of different tagged nucleic acid molecules is counted.

In the disclosed method, each sequence read generated from a tagged nucleic acid molecule comprises two parts, or subsequences. The first part corresponds to the tag, which identifies the tag (and the sample tag if samples are pooled). The second part corresponds to a nucleic acid in the sample which is mapped to a location in the genome (or to a transcript RNA molecules are being counted). After deconvoluting by sample tag, the number of different tagged nucleic acid molecules mapped to each location is counted. There are two separate methods of counting, and each can be combined for greater accuracy and determination of confidence.

The first counting method is called "maximum tagged nucleic acid molecule number." The number of different tagged nucleic acid molecules at a given location cannot exceed the true (absolute) copy number. Therefore, for a given region comprising multiple locations, the maximum copy number of the region is not less than the maximum number of different tagged nucleic acid molecules mapped to any location in that region. The maximum number of different tagged nucleic acid molecules centered about a moving window of a fixed number of locations can be taken as the measurement of true copy number of the window. This will provide at worst an underestimate of the maximum true copy number for that window, and never an overestimate. The set of maximum number of different tagged nucleic acid molecules is one type of copy number profile.

The counting method described above is most accurate when the processing efficiency is excellent and the number of molecules mapped to each location is less than the number of tags. Under such conditions virtually each molecule in the sample is tagged and counted, and the true count can be derived. But there is a second method.

The second counting method is called "total different tagged nucleic acid molecules," and is useful, for example, when tagging efficiency is low. The total number of different tagged nucleic acid molecules within a region of a fixed number of locations will be, within a statistical counting error, a monotonic function of true copy number, regardless of the efficiency of tagging. Low efficiency of tagging merely increases the statistical error. The relative copy number of a region can be estimated by comparing the total number of different tagged nucleic acid molecules mapped to the region to, for example, the mean value of tagged nucleic acid molecules mapped to other regions of the genome which have a comparable number of locations.

If the number of molecules at a location on a genome or cDNA library exceeds the number of tags, and tagging is too efficient, copy number information can not be recovered. Rather, the total number of tags at each location would merely be measured. There are at least three ways to remedy this condition: 1) diminish the efficiency of the first step of the process, for example by reducing the reaction time; 2) reduce the amount of sample; and 3) increase the total number of tags. For example, if the length of the tag were nucleotides, there are $4^N$ possible tags. For N=15, there are approximately $10^9$ tags, easily in excess of the number of molecules per location.

The collection of reads lend themselves to modeling the power of inference. For each location, there exists the number of tagged nucleic acid molecules observed, and for each species of tagged nucleic acid molecule, the number of times it was observed. With a good estimate of the input, the number of genomes, critical parameters can be accurately deduced because the vast majority of the copy numbers are two per genome. The limiting case of single cell analysis lends itself to the most accurate modeling, with the proportion of null reads enabling the inference of the probability, theta, that a single molecule at a location is detected. Theta is a function of the efficiency of tagging, the efficiency of amplification and processing, and the read depth.

Using the language invented of the WGA reaction, in the specific protocol described here, all first order derivative DNA molecules (i.e., first copies) are tagged, with no new tags introduced when subsequent order derivatives are created. This enables the "counting" of original molecules, alleles in the case of genome analysis. This method is referred to herein as "varietal counting." As long as sequence depth is sufficient, subsequent amplification or methods of trapping that enrich for regions of interest, or the combination, cannot distort the count. Pooling from multiple cells becomes a natural extension of this method, which improves efficiency, increases throughput and decreases costs.

Tags

The tags are nucleotide sequences with constant portions and variable portions. The length of the constant portion and the length of the variable portion may be the same or different. The length of the tags within a plurality of tags is typically, but not necessarily, the same for all tags. In an embodiment, the total length of a tag is less than 100 nucleotides.

The constant portions are used to aid in the tagging of nucleic acid molecules. For example, the constant portion may contain a nucleotide sequence which allows hybridization to a poly-N tail added by a terminal transferase. The constant portion may also be used to aid in manipulation of the tagged nucleic acid molecules. For example, the constant portion may contain a sequence which is a primer binding site useful for PCR amplification. The constant portion may also be used to identify a sample if there are multiple samples being processed in parallel, i.e., the constant portion may contain a sample tag.

The sequence of individual tags does not need to be known prior to generating tagged nucleic acid molecules. A plurality of tags may have variable portions whose sequences are elucidated for the first time during sequencing. The variable portion of a tag may be a sequence of nucleotides where each nucleotide is individually one of A, T, C, or G, or one of any two of A, T, C, and G, or one of any three of A, T, C, and G, i.e. the variable portion of a tag may consist of only two or three species of nucleotides. Tags may be designed such that the variable portion has a random sequence. Tags may be designed such that the variable portions are constructed from a set of dinucleotides or trinucleotides.

Tags may be associated with nucleic acid molecules by using, singly or in combination, ligation, nick-ligation, terminal transferase, hybridization, priming, and the like. For example, nucleic acid molecules may be cut with a restriction endonuclease(s), treated with a terminal transferase to add a poly-N tail, hybridized to a tag molecule, and then nick ligated to form a tagged nucleic acid molecule. Specific methods of generating tagged nucleic acid molecules are discussed in detail below.

Tagging With the Aid of a Terminal Transferase

Figure 8:
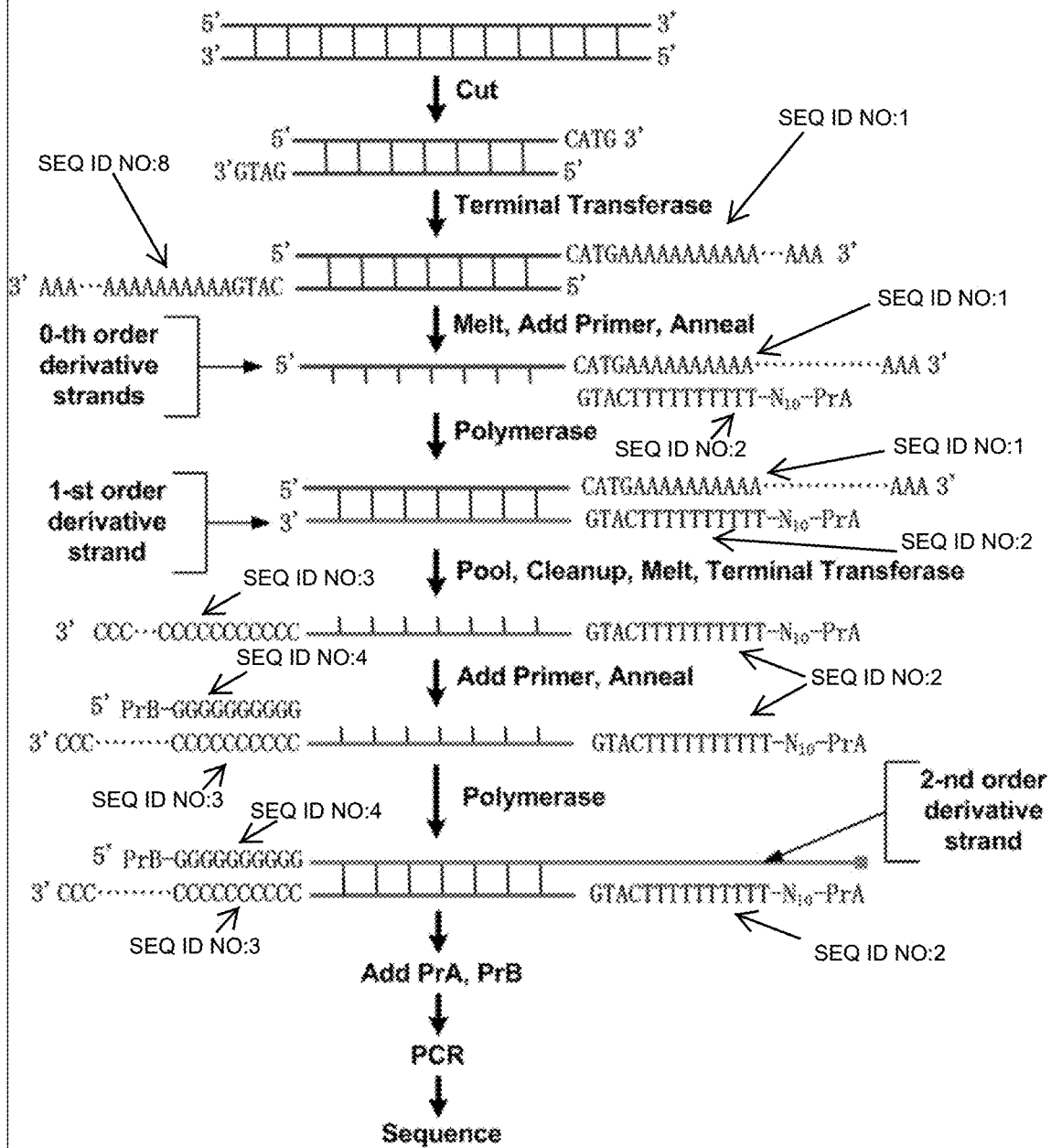

FIG. 8 illustrates one embodiment of this method, where the $N_{10}$ designates an oligonucleotide having a tag component and a sample tag component. The first six nucleotides (4096 possible sequences), randomly generated, provide the tag component, and the last four nucleotides (256 choices) are chosen to encode the micro-well, and, hence, a sample tag. The lengths of the tag and the sample tag can be changed to suit needs, and are not limited to a total of ten nucleotides. The lengths are chosen for illustration. The sample tag allows pooling, with deconvolution occurring afterwards. The combination of a tag with a nucleic acid molecule from the input sample provides an essentially unique tagged nucleic acid molecule for the first derivative strand, that can only with very low probability be replicated by chance from another like molecule (a chance of roughly 1/N where N is the number of available tags). In the end, multiple copies of sequence-identical molecules in the input sample are each individually counted. In applications to mRNA counting, the length of the tag component can be increased to accommodate possibly thousands of transcripts from the same gene.

Although there are multiple embodiments of the basic method besides the one illustrated in FIG. 8, the embodiment illustrated in FIG. 8 has several useful design features. First, it avoids the use of ligases (an alternate method for associating a tag with a nucleic acid molecule), which has been found to be an inefficient reaction. Instead, this embodiment uses terminal transferase (TTase), which is a robust enzyme from which high efficiency is expected. Second, once the tag and sample tag are incorporated into the first derivative DNA strand, micro-wells can be pooled and the subsequent steps carried out more efficiently in larger volumes with larger numbers of molecules, possibly with the addition of carrier nucleic acids. Because of a clean-up step, removing free adaptor, no more unique first order derivative strands with tags can be created, and second order strands can be arithmetically expanded if found to be useful. Third, the method extends immediately from DNA to mRNA. Rather than cleaving and adding a polynucleotide tail with terminal transferase, the naturally occurring polyA tail of mRNAs can be utilized. Fourth, it is easy to see how to combine analysis of both RNA and DNA from the same cell with this schema. Instead of tailing DNA with A, it can be tailed with, for example, C, thus distinguishing the DNA from the RNA. DNA and RNA derivatives can either be read together in the same sequencing runs, or separately by amplification using their differing PCR primer adaptors. Fifth, by using a longer sample tag, sequences belonging to a particular cell can be preferentially amplified for deeper study when warranted.

This method can be applied to assessing DNA methylation. After the first order derivative strands are made, the duplex DNA can be pooled from multiple samples. These molecules will be hemi-methylated, and still retain epigenetic marks. Therefore they can then be separated into methylated and unmethylated samples either by cleavage with methylation sensitive restriction enzymes, or by partitioning with antibodies or methyl-C binding proteins directed to methylated (or hydroxyl methylated) cytosine. Error rates will be measured based on expectations from regions of known methylation state.

Tagging by Ligation

In another embodiment of the invention, adaptors with tag(s) can be ligated to sample DNA or RNA that has been converted to DNA. In the second step these molecules can be pooled (or not) and amplified for sequencing. In the third step the numbers of each different tagged nucleic acid molecule of each locus (or mappable sequence read) are compiled, giving statistics from which copy number can be inferred.

In another embodiment, to measure RNA, RNA is first converted to DNA using methods that produce a single double stranded molecule for each RNA in the sample. (For example, prime with oligo dT and reverse transcriptase, followed with random priming and Kienow polymerase.) The procedures for analyzing DNA can then be followed.

In another embodiment, the sample DNA can be sheared and the ends prepared for ligation. However, there are three major advantages to cleaving with one or more restriction endonucleases (RE). The first is that the expected number of tagged nucleic acid molecules at each location can be precisely predicted from the starting number of cells in the sample, or conversely the number of cells in the sample inferred from the expected number of tagged nucleic acid molecules per location. The second is that the expected complexity of the product is reduced, enabling copy number determination from fewer sequence reads. The third are certain advantages in the flexibility and functionality that can be built into the tags.

In an embodiment, sample nucleic acid is cleaved with a specific restriction enzyme and sample molecules are ligated to tagged (and sample tagged if appropriate) oligonucleotide adaptors which contain sequences that allow FOR amplification. There are various designs for these adaptors, and also alternatives to FOR (such as WGA), based on the functionalities built into the tags. Some of these additional functionalities are discussed below.

The ligated molecules now are essentially unique, the ligated molecules each being the combination of a substantially unique tag and DNA sequence to which they were ligated. Further amplification may distort the yields of molecules, but will not create new tags (although some may be lost by statistical processes which are readily modeled during analysis).

Through sequence error during processing, the tag may very occasionally mutate, creating the appearance of a new tagged nucleic acid molecule. But if the set of tags are sufficiently large, the tagged nucleic acid molecules will generally differ at more than one nucleotide, and so tagged nucleic acid molecules that differ by a single nucleotide can (optionally) be ignored when counting.

For single cells, individual cells are loaded at most one per microwell. The nucleic acid is then prepared in wells, and the molecules tagged. Once tagged they can be pooled for further processing, which greatly improves the uniformity and efficiency of DNA amplification methods.

In yet another embodiment, DNA is cut, and adaptors are ligated to both ends of each fragment, enabling them to bP amplifiable by PCR. To avoid adaptor-adaptor self ligation, double stranded adaptors without 5' phosphorylation can be used, so an adaptor is ligated on one strand only at each end of the cleaved sample DNA. Then the molecules are pooled, and treated as for representations: the shorter single strand adaptor is melted off at elevated temperature but well below the Tm for the sample duplex, the ends of the double stranded DNA filled in with Klenow polymerase, unligated adaptors removed, and then the sample is PCR amplified.

In the preceding embodiment, adaptors are used not only for tagging but also for amplification. Adaptors are for identifying each molecule individually. They can also be used for amplification, as described above, or for other uses (see below). Because in the above embodiment adaptor ligation at both ends of sample fragments is required for amplification, the yield may be diminished. To improve yield, the method can work with molecules that have an adaptor at one end only.

In one embodiment, the reactions are performed as before, but tags do not contain sequences enabling PCR. Prior to PCR, but after an optional pooling, fresh adaptors (different composition and without tags) are ligated so that molecules with only a single tag adaptor can be amplified and eventually counted. If the original tag has a selection sequence, molecules with the tag adaptor before sequencing can be optionally enriched by hybrid selection.

In another embodiment, initial adaptors are designed with a phosphorylated 5' end and a 3' dideoxy end, so that the initial ligation occurs to the opposite strand as described in the embodiment above. (Instead of using an RE with a 5' overhang, one which leaves a 3' overhang may be preferred.) After removal of unligated adaptors, there follows several rounds of arithmetic amplification, followed by tailing molecules with dT using terminal transferase, and amplification of the processed sample DNA by PCR.

In another embodiment, DNA from sample is labeled as before, pooled if required, and unligated adaptors removed from the reaction. The reaction is subject to whole genome amplification (WGA), and the product of WGA is used to make sequencing libraries. For this embodiment, the initial adaptors may also contain: (A) cleavage sites for ease of making sequencing libraries; and (B) a sequence large enough for optional enrichment by hybrid selection prior to making libraries for sequencing.

In the embodiments just described, it is assumed that the tag is double stranded. The production of a great variety of double stranded molecules is not completely straightforward. In one embodiment, single strand DNA is synthesized as type I and type II. Type II has three sets of functionalities A, B, C, and D. Functionalities B contain the tag sequence, C the adhesive ends with a RE site, and D the buffer. The B will contain some length of runs with random sequence, for example 10 nucleotides with a total complexity of $4^{10}$, or about $10^6$ possible sequences. Type I oligo will be complementary to type II at functionality A, the two joined and annealed, and then extended with polymerase to create a double stranded molecule. After cleavage with the RE site, the resulting double stranded molecule is the tag used for the subsequent tagging of the sample.

Additional methods for producing single and double stranded oligonucleotides suitable for use as tags are known in the art, for example, in U.S. Pat. Nos. 5,639,603 and 7,622,281, U.S. Patent Application Publication No. 2006/0073506 and Parameswaran et al. (2007) (7,5,8,4).

Nick-Ligation

In this embodiment of the invention, 3'OH ends of nucleic acid molecules, e.g., segments of genomic material or mRNA transcripts, are first extended with terminal transferase, adding a poly-N tail. Primer adaptors are then annealed to the poly-N tails and the resulting duplex with a nick is sealed with DNA ligase. This series of reactions is much more efficient than a single step double stranded ligation. The resulting product is amplified by PCR. This method has been successfully used with as little as 1 ng of DNA. Tagged nucleic acid molecules generated using the nick-ligation method can be generated from a single cell DNA, and then pooled prior to PCR. Pooling from 100 cells yields the DNA concentration needed for successful amplification. Sample tags can be added in the nick ligation step, and this is readily achieved (see FIG. 9).

Technology for Inexpensive Assay of Regional Markers

The above description is of methodology designed to measure copy number and mutational loads throughout much of the genome in single cells. But the application of discoveries, once made, of predictive markers for outcome or therapeutic response will not require whole genome information. Our present outcome markers are in fact copy number markers at very specific loci. Essentially the same methodology as disclosed hereinabove can be employed to make these assessments very affordable. Consider, for example, the case where it is desirable to assess a large study for the predicative power of a set of N markers, and these markers are copy number markers that can be assessed by varietal counting. In principle, sample coding, pooling, and parallel capture and sequencing can be used to assay a large number of samples in a single sequencing lane. The major difference is that we are not restricted to minute quantities of DNA, so WGA is not needed, and assays will be more robust. We have shown in our autism work that excellent copy number data can be obtained from read depth after capture. Thus we can use direct library preparation with just sample tags. The target area for capture is likely to be different and smaller than the exome. Thus we can pool more samples per sequencing lane, and the sequencing costs for assaying hundreds of markers in hundreds of samples can be reduced. Of course, there are costs as: with the development and testing of the capture reagents, and the cost of the capture itself, and these are not negligible, but if a test were to come into widespread clinical use, it would be inexpensive, and this is one of our major objectives. There is a clear alternative, namely creating a bank of region specific PCR primers with tags and sample tags. The tags would be necessary because random unique ends created by shearing would not be available for counting based methods. This alternative plan could be less expensive and more robust than capture (see FIG. 10).

Single Cell RNA Measurements

Several methods have now been published whereby researchers have profiled the RNA content of single cells by sequencing (Tang et. al., 2009). This is potentially a very powerful method for analysis of tumor cells. A varietal counting method could be very useful for RNA profiling from single cells, and for the seine reasons that it is useful with DNA. When variety is not introduced by nucleic acid processing varietal counting provides a way to avoid the distortions created by PCR. RNA and DNA can be analyzed from the same cells. The DNA analysis enables us to cluster cells into stromal and tumor subpopulations, and this in turn facilitates the interpretation of the RNA profiling. As an example of utility, suppose one is interested in searching thousands of circulating cells, or cells from a biopsy, or from the margins of a tumor, for rare tumor cells. DNA copy number can facilitate its identification, and the RNA from that cell can then be reliably used to infer additional properties, such as the tissue of origin. This combination is especially powerful for the early detection of the new incidence or recurrence of cancer.

Examples

Methylation Sequencing

Currently, high throughput sequencing requires physical purification of sub-genomic regions of interest in order to obtain high coverage of those regions. The method of sequence capture has been applied to examine methylation in large sets of CpG islands at the sequence level. Methylation sequencing is based on the conversion of C residues to T using bisulfite reagents, with methylated C's detected as those protected from C to T conversion. This means either that sequence capture must take place before bisulfite treatment, which requires more starting DNA than is available for patient specimens, or that sequence capture must be designed to accommodate the C to I conversion. The bisulfite based sequencing method used herein adopts the latter and so is suitable for high throughput single molecule sequencing by either the Illumina or Roche 454 methods, using as little as 100 ng of input DNA. The sequencing method depends on hybrid capture of bisulfite treated DNA followed by sequencing through the Illumina Solexa sequencer and mapping back to the genome using an algorithm developed Dr. Andrew Smith (19). It was observed that CpG islands can exhibit multiple different levels of methylation, from imprinted (allelic) to randomly partially methylated, to completely methylated or unmethylated. In particular, one observation that is important for this invention is that many islands switch from completely unmethylated in normal tissues to virtually completely methylated in matched tumor tissue ("DNA-methylation switch domains"). FIG. 3 shows three examples of the simplest cases in normal cells versus the breast cancer cell line MDA-MB-231: stably unmethylated (A and B); the AIX gene, switched from unmethylated to completely methylated (C and D); and a case, SSTR4, where only a segment of the island is switched (F and F). This complete switch makes it possible to detect rare tumor cell DNA in bodily fluids or other cell populations using nested PCR of bisulfite treated DNA and opens up the possibility of a creating a method for the early detection of recurrence in the form of circulating metastatic cells.

Comparative Genomic Hybridization (CGE) by High Throughput Sequencing

Until now the most economical method for high resolution genomic analysis has employed some form of microarray. The rapid rise of 'next generation' DNA sequencing is changing that landscape. Both the Illumina (Solexa) and Roche 454 instruments can provide millions of individual sequence reads randomly distributed across any input DNA (Craig et al., 2008). The depth of coverage of these technologies depends on the total length of the input DNA, from whole genome (large breadth, lower depth) to narrowly focused regions achieved by hybrid capture of specific sequences (narrow breadth, higher depth) (Albert et al., 2007; Hodges et al., 2007; Okou et al., 2007). Converting sequencing reads to copy number analysis is a matter of mapping reads and then put them into 'bins' of a certain size, depending on the purpose, counting up the numbers in the bins and performing appropriate statistical analysis to define copy number change breakpoints.

Sequence counting was applied to the degraded formalin-fixed paraffin-embedded (FFPE) DNA that was available from retrospective clinical trials with very encouraging results. FIG. 4 displays a comparison of microarray and sequence counting results in a region around Her2 on chromosome 17 for a 10 year old paraffin-embedded clinical trial sample JZ33. The gray and orange points are (respectively) the raw ratio data for 244K Agilent microarray and one lane of Solexa sequencing reads divided into 30K bins. Note that the sequencing (orange) track shows significantly less noise. The green and blue lines are the result of segmenting each data type. The segments are generally concordant, but the sequence counting method reveals a somewhat more detailed pattern. Another feature of note from FIG. 4 is the robustness of our segmenting program, irrespective of the variation of noise in the two sets of raw data.

The efficacy of sequence counting on FFPE DNA and the rapidly decreasing cost of DNA sequencing in general provides an opportunity to convert our previous microarray methods to a highly flexible and scalable platform for breast cancer genome diagnostics. Both the breadth of DNA to be sequenced and the size and location (and therefore resolution) of individual bins can be easily adjusted to fit the particular loci to be assayed.

Single Cell Microarray and Sequencing

A representation of DNA amplified from single cells was used for genomic profiling by 'sequence counting'. As a preliminary step in developing that technology, DNA was amplified from batches of 1, 10 and 100 cells of the cell line SKBR3 using the Whole Genome Amplification (WGA) Kit from Sigma-Aldrich and compared these amplified representations to equivalent microarrays on the same format done with a standard SKBR3 DNA prep. Individual cells were picked from adherent culture dishes using a cell transfer micropipette. After random WGA1 amplification the DNA preps were digested with DpnII and AluI, adaptors added and only DpnII fragments without AluI sites were amplified by PCR. These representations were labeled and applied to ROMA custom microarrays with 390,000 probes designed to detect DpnII fragments of appropriate size across the genome. The idea was to test how reproducible this two step process would be when only 2-6 chromosomes are present in each single cell preparation (SKBR3 is roughly triploid).

The results are shown in FIG. 5, presenting a comparison of the segmented profiles of a batch preparation of SKBR3 DNA (FIG. 5A) against our normal male reference cell line (SKN-1) and three independent single cell DNAs (FIG. 5B,C,D). A visual inspection of these profiles makes it clear that after segmentation, the results for single cells are virtually identical to a standard. DNA, leading us to have confidence that sequencing DNA from a representation will yield useful results. Although the raw ratio data is not presented here, we note that the standard deviation of the ratio data is much higher for the three single cell experiments (0.706, 0.725, 0.676) than for a batch DNA preparation (0.313). The extra noise does not adversely affect segmentation, although in certain regions very fine detail may be lost (red arrow in FIG. 5A). This is comparable to other WGA1 experiments such as the one depicted in gray in FIG. 4. In this light it is also worth noting that our particular use of the WGA1 method does not depend on absolutely uniform amplification across the genome. We benefit from the redundancy of data that we gain from segmentation to identify breakpoints. Even if only half of the potential fragments from a single cell were amplified in a given reaction, we would still obtain useful data.

Sequencing Across Chromosome Breakpoints

One of the methods for the detection of rare tumor cells, in lymph nodes, blood or other bodily fluids is the amplification or sequencing of unique breakpoints resulting from deletions and/or translocations that occur during breast tumor development. Although events such as deletions and duplications are apparent from array CGH, the actual structure underlying the copy number changes is not.

The DNA sequences surrounding 22 breakpoints from two breast cancer cell lines were enriched by hybrid capture on custom microarrays as described by Hodges et al (20). Following hybrid capture, the enriched DNA was amplified and prepared for 'paired end' sequencing on the Illumina GA2 instrument. Paired end sequencing yields approximately 36 bp of sequence from each end of a single DNA molecule (after preparation for sequencing, each molecule is approximately 200 bp in length), and those sequences are then mapped back to the consensus genome. For a molecule from a normal, non-rearranged region the two matched reads should map approximately 130 bp apart. In contrast, at the edges of a deletion, the two reads from a single molecule would be separated on the map by the width of the deletion, or in the case of a translocation, would map to another chromosome. These are referred to as 'bridging fragments' because they connect regions not normally adjacent to one another. Examples of two such bridging fragments are shown at the top of FIG. 6, along with the original CGH pattern, and graphs of the distance between paired ends (blue) and the total number of reads (red) across the capture region (X axis). By mapping the exact location of a breakpoint, highly sensitive and specific probes that will distinguish tumor cells from large numbers of normal cell can be prepared. Of 22 regions displaying deletions captured from cell lines T47D and MDA-MB-436, 15 behaved as simple deletions from which unique 'bridging fragments' could be identified as in FIG. 6. Two additional sites 'jumped' to different chromosomes indicating translocations. The other 5 sites involved repeated sequences on one of the paired for which the identification of the exact breakpoint was not possible and which would not be suitable for creating unique probes.

Copy Number Profiling Using Varietal Tags on Restriction Enzyme Fragments.

As one illustration of varietal counting, copy number information was obtained using a "total different tagged nucleic acid molecules method.", DNA fragments were first associated with tags by using terminal transferase and nick-ligation (FIG. 9). Genome DNA was obtained from the cell line SKBR3. DNA (2 µg) was digested by NlaIII, resulting DNA fragments with 4 bp, "CATG", 3' overhangs. This 3'OH end was extended with terminal transferase by adding a poly-A tail. One of primer adaptors was designed to have tags, 12 Ts and CATG at the 3' end, so it could be annealed to the 3' ends of the DNA fragments with a nick site (FIG. 9, Product 3). This nick site was ligated by DNA ligase, forming duplex DNA fragments with tags. Another primer adaptor was then added to these duplex DNA fragments by one cycle of PCR (FIG. 9, Step 5), allowing the resulting products of this reaction to be further amplified by followed by sequencing (Illumina/Solexa). Then, by mapping the subsequence of each tag associated sequence read to a location on the genome, the number of DNA fragments (assigned to the same genomic location) with different tags was counted.

We have previously obtained copy number profiles of SKBR3 genomic DNA from a million cell library, by sequencing and sequence counting. FIG. 11 compares the use of varietal counting (a "total different tagged nucleic acid molecules method") with 'sequence counting' for analyzing copy number data, genome-wide (FIG. 11A) and partial-genome (FIG. 11B). The essentially equivalent result obtained using varietal counting illustrates that by adding varietal tags to DNA fragments before PCR one can use varietal counting as described herein to reliably obtain copy number information unaffected by amplification distortion.

Data analysis for the procedure described above employed a modification of the 'bin-counting' method because the NlaIII restriction sites are not distributed evenly in the genome. Therefore, in order to ensure equal weight for each of the 50K bins, the bin boundaries for this experiment were designed to encompass and equal number of NlaIII fragments sized between 100 bp and 250 bp, the size range from which the lumina libraries were made.

Discussion

Single cell data is much more informative than data obtained from multiple cells, for example from array hybridization of multiple sections of a primary tumor. First, one can afford to analyze many more genomes by multiplex single cell sequencing than by array hybridization (on the order of a hundred single cells versus a dozen sections). Second, one is able to directly assess the exact proportion of cells in a region of a tumor that are malignant. Third, one is able to make a far more detailed analysis of the temporal order of genetic lesions, since one will not be looking at the average state of a population. Fourth, one is able to assess whether tumor heterogeneity is of the anatomically segregated or the co-habitation type, or both.

The invention described herein may be used to determine the original genome copy number (or the gene expression profile) of a sample without amplification distortion. All measurements of copy number or gene expression, especially involving multiple samples, are potential applications. Samples can be nucleic acids derived from single cells or populations of cells. The invention can be used to study cellular heterogeneity in tumors or normal populations of cells.

The invention may be used to generate a genomic profile of a cell, e.g., a cancer cell, or population of cells. From the genomic profile it can be determined if specific genes are amplified or deleted. When the sample is derived from expressed RNA, and the regions are expressed genes, the relative counts comprise an expression profile. From the expression profile the tissue of origin of a cancer cell can be identified. When the sample is a mixture of genomes from different species, and the genomic regions distinguish the different species, the relative counts comprise a census of those different species. For example, from a census we can determine the population of microbial flora and relate the same to disease.

One of the advantages of the use of tags is that it allows the use of restriction endonuclease fragments in genome analysis. Counting methods for genome copy number determination use counts of independent reads. Two reads are not considered independent if they are the result of DNA amplification occurring during sample processing. Typically, this entails shearing sample DNA fragments, and the position of ends of the fragments are used to disambiguate FOR duplicates. If two DNA reads have the same ends, they could be PCR duplicates, and not independent, so they are counted as only one true read. One cannot disambiguate restriction fragments this way, because two reads of the same fragment will have the same ends. However, by the addition of tags, independent reads can be distinguished, if they are added before any amplification step, as they will have different tags. By contrast, if two reads of the same genome region have the same tag, they are highly likely to be PCR duplicates, and not independent.

The ability to use sequence of restriction fragments in genome analysis can be exploited to reduce the cost of determining copy number profile, much as performing ROMA facilitates genome analysis. By size selection of fragments, one can sample the genome at, greater depth at fewer loci, and still obtain a high resolution copy number profile but with fewer reads and therefore at lower cost. This is the essence of representation, and results in complexity reduction, the central element of ROMA. In ROMA, the analysis of the representation is done by hybridization to arrays, and here the representation is analyzed by sequencing.

Further complexity reduction can be achieved by sequence capture. The sequence capture can be designed specifically for the fragments that can be predicted by in silica methods to map to the regions where one wants copy number mutation. In this way one can target special regions of the genome, such as the exome, or known cancer genes. Very little sequence of the sample is then needed for copy number determination, and samples can be multiplexed at a great cost saving.

The invention disclosed herein may also be used to determine the proportion of components a mixture. For example, suppose one possesses a set of reagents, such as antibody molecules, that bind to a set of substrates, such as different proteins, and one desires to detect the relative proportion of those substrates in a sample, such as blood. First, one covalently combines a tag having a sample tag with each reagent, where the sample tag portion identifies the reagent, and the varietal tag will be used in counting. The tagged reagents are then combined with the sample, and reagents that combine with substrates are physically separated. For example, the substrates may be biotinylated before being mixed with reagents, then reagents combining with substrates separated by avidin affinity chromatography. The tags are amplified by PCR and sequenced, effectively yielding relative counts for each reagent species and therefore each substrate. In this case, the constant portions of the tags include the sample identifier and nucleotides used for amplification.

The invention provides the following advantages: (1) the method is simple; (2) with statistical analysis the confidence of a measurement can be determined with great accuracy; (3) this is a sequence based method, which in the long run will be cheaper than arrays; (4) long read lengths are not necessary, providing savings; (5) because tagged nucleic acid molecules are counted, many processing methods that create distortion in yields can be applied without major loss in the tagged nucleic acid molecule count; (6) among these processing methods are hybrid selection (aka capture microarrays), which restrict the sequence information to regions of importance, and thus reduce cost by reducing the total number of reads per sample needed for determination of the desired information; (7) the molecules from one sample can be combined with tags and a sample tag, creating sample tagged nucleic acid molecules which can then be pooled, and after processing and sequencing, the sample tags decoded, giving a profile for each sample; (8) pooling adds efficiency and uniformity; (9) the samples can be individual cells, yielding large numbers of single cell measurements cheaply.

The invention described herein has clinical applications as described above, including: (1) determination of the genomic heterogeneity of tumors; (2) detection of tumor cells in needle biopsies, in particular an assessment of the heterogeneity of the cells in a biopsy; (3) assessment of the spread of a cancer to regional lymph nodes; and (4) detection of malignant cells in sites such as blood and bone marrow. The presence of cells with the molecular signature of the primary in the blood or bone marrow opens up the possibility of using more general single cell/molecule assays as a first line of defense in the early detection of cancer, i.e. breast cancer in women at risk.

When there is radiological evidence of a breast mass, the patient most commonly undergoes fine needle biopsy, which is examined by the pathologist who makes an assessment of the malignancy of the mass. Because needle aspiration destroys the histology of the biopsy, one of the pathologist's canonical tools for assessing malignancy is not available. Single cell sequencing would not only more accurately predict the presence of malignant cells, but also give what we might call "genomic staging." Is the tumor a simplex type of complex type? Is it mongenomic or polygenomic? Are there critical loci that are amplified or deleted that might immediately suggest a preoperative therapy?

The single cell/molecule approach allows the assessment of the spread of cancer to regional lymph nodes and to establish the DNA-methylation states at switch regions.

Successful application of single cell/molecule detection in the above contexts will lead to application to the detection of cancer recurrence, and the measurement of cancer load. Detection of recurrence at the earliest possible time may prolong survival for a large class of patients by earlier intervention than they would otherwise receive. Moreover, if cancer load were monitored in the patient, even before the site of the cancer growth is discernible by imaging, then one could measure the response of the cancer to a variety of therapeutic measurements. That is, the most effective choice of therapy could be determined empirically in the patient.

Additional applications exist in the diagnosis and selection of treatment for patients with auto-immune diseases, and in vitro fertilization (IVF) screening of pre-implant embryos for genetic defects such as trisomy-21.

REFERENCES

The disclosures of the following references in their entireties are hereby incorporated by reference into this application.
1. Pinard R, de Winter A, Sarkis G J, Gerstein M B, Tartar K R, Plant R N, et al. Assessment of whole genome amplification-induced bias through high-throughput, massively parallel whole genome sequencing. BMC Genomics. 2006; 7:216. PMCID: PMC1560136.
2. Klein, C. et al. Comparative genomic hybridization, loss of heterozygosity, and DNA sequence analysis of single cells. PNAS. 1999; 96, pp. 4494-4499.
3. Stoecklein, N. et al. SCCMP Is Superior to Degenerated Oligonucleotide Primed-Polymerase Chain Reaction for Global Amplification of Minute Amounts of DNA from Microdissected Archival Tissue Samples. American Journal of Pathology. 2002; 161(1):43-51.
4. Parameswaran et al. A pyrosequencing-tailored nucleotide barcode design unveils opportunities for large-scale sample multiplexing. Nucleic Acids Research. 2007; 35(19): e130.
5. U.S. Pat. No. 7,622,281, Ronaghi et al.
6. Eid at: al. Real-Time DNA Sequencing from Single Polymerase Molecules. Science. 2009; 323:183-138.
7. U.S. Pat. No. 5,639,603, Dower et al.
8. U.S. Patent Application Publication No. 2006/0073506, Christians et al.
9. Navin N, Krasnitz A, Rodgers L, Cook K, Meth C, Kendall J, et al. Inferring tumor progression from genomic heterogeneity. Genome Res. 2010; 20(1):68-80. PMCID: 2798832.
10. Fisher B, Redmond C K, Fisher E R. Evolution of knowledge related to breast cancer heterogeneity: a 25-year retrospective. J Clin Oncol. 2008; 26(13):2068-71.
11. Langmead B, Trapnell C, Pop M, Salzberg S L. Ultrafast and memory-efficient alignment of short DNA sequences to the human genome. Genome Biol. 2009; 10(3):R25. PMCID: PMC2690996.
12. Saitou N, Nei M. The neighbor-joining method: a new method for reconstructing phylogenetic trees. Mol Biol Evol. 1987; 4(4):406-25.
13. De Baetselier P, Roos E, Brys L, Remels L, Gobert M, Dekegel D, et al. Nonmetastatic tumor cells acquire metastatic properties following somatic hybridization with normal cells, Cancer Metastasis Rev. 1984; 3(1):5-24.
14. Duelli D M, Padilla-Nash H M, Berman D, Murphy R N, Ried T, Lazebnik Y. A virus causes cancer by inducing massive chromosomal instability through cell fusion. Curr Biol. 2007; 17(5):431-7.
15. Jorgensen H F, Adie K, Chaubert P, Bird A. P. Engineering a high-affinity methyl-CpG-binding protein. Nucleic Acids Res. 2006; 34(13):e96. PMCID: PMC1540740.
16. Meehan R R, Lewis J D, Bird A P. Characterization of MeCP2, a vertebrate DNA binding protein with affinity for methylated DNA. Nucleic Acids Res. 1992; 20(19): 5085-92. PMCID: PMC334288.
17. Huang J., Pang J., Watanabe T., Ng H K, Ohgaki H. Whole genome amplification for array comparative genomic hybridization using DNA extracted from formalin-fixed, paraffin-embedded histological sections. J Mol Diagn. 2009 March; 11(2):109-16. Epub 2009 Feb. 5.
18. Talseth-Palmer B A, Bowden N A, Hill A, Meldrum C, Scott. R J. Whole genome amplification and its impact on CGH array profiles. BMC Res Notes. 2008 July 29; 1:56.
19. Hodges H, Smith A D, Kendal J, Xuan Z, Ravi K, Rooks M, Zhang M O, Ye K, Bhattacharjee A, Brizuela I L, McCombie W R, Wigier M, Hannon G J, Hicks J B. High definition profiling of mammalian DNA methylation by array capture and single molecule bisulfite sequencing. Genome Res. 2009 September; 19(9):1593-605. Epub 2009 Jul. 6.
20. Hodges E, Xuan Z, Balija V, Kramer M, Molla M N, Smith S W, Middle C M, Rodesch M J, Albert T J, Hannon G J, McCombie W R. Genome-wide in situ exon capture for selective resequencing. Genet. 2007 December; 39(12):1522-7. Epub 2007 Nov. 4.
21. genome.ucsc.edu/index.html?org=Human&db=hg19&hgsid=171216665
22. Miner B. E., Stager, R. J., Burden, A. F., Laird, C. D., Hansen R. S. Molecular barcodes detect redundancy and contamination in hairpin-bisulfite P. R. Nucleic Acids Research, 2004:32(17):e135.
23. U.S. Pat. No. 7,537,897, issued May 26, 2009 (Brenner et al.).
24. McCloskey M. L., Stager, R., Hansen, R. S., Laird, C. D. Encoding PCR Products with Batch-stamps and Barcodes. Biochem. Genet. 2007:45:761-67.

What is claimed is:

1. A method comprising:
   a) obtaining segments of genomic nucleic acids from a sample containing the genomic nucleic acids;
   b) randomly tagging the segments of genomic nucleic acids with different nucleic acid tags, thereby generating unique tagged nucleic acid molecules from the segments of genomic nucleic acids, such that each of the unique tagged nucleic acid molecules comprises a segment of the segments of the genomic nucleic acids from step (a) and a nucleic acid tag of the nucleic acid tags;
   c) subjecting the unique tagged nucleic acid molecules to a polymerase chain reaction (PCR), thereby generating copies of the unique tagged nucleic acid molecules;
   d) generating tag associated sequence reads by sequencing the copies of the unique tagged nucleic acid molecules of step (c);
   e) assigning each of the unique tagged nucleic acid molecules to a location on a genome by mapping each of the tag associated sequence reads of step (d) to a location in the genome; and
   f) in a plurality of locations in the genome, obtaining relative copy number information of the genomic nucleic acids from the sample based on the number of unique tagged nucleic acid molecules that have been assigned to each of the plurality of locations in the genome.

2. The method of claim 1, wherein the polymerase chain reaction is performed in the presence of region specific PCR primers.

3. The method of claim 1, wherein the unique tagged nucleic acid molecules differ at more than one nucleotide or wherein the sequences of the nucleic acid tags are known prior to said generating unique tagged nucleic acid molecules from the segments of genomic nucleic acids.

4. The method of claim 1, wherein the segments of the genomic nucleic acids are produced by mechanical shearing, heating, or sonicating the genomic nucleic acids from the sample.

5. The method of claim 1, wherein the nucleic acid tags comprise a sample tag or a sample tag set.

6. The method of claim 5, wherein the unique tagged nucleic acid molecules are pooled with a plurality of unique tagged nucleic acid molecules having a different sample tag prior to the PCR or prior to said sequencing of the amplified tagged nucleic acid molecules product of step (c).

7. The method of claim 6, further comprising deconvoluting the tag associated sequence reads by grouping the tag associated sequence reads.

8. The method of claim 1, wherein the nucleic acid tags are double-stranded.

9. The method of claim 1, wherein the unique tagged nucleic acid molecules are subjected to hybrid capture prior to the PCR or the amplified tagged nucleic acid molecules produced in step (c) are subjected to hybrid capture prior to step (d).

10. The method of claim 1, wherein the genomic nucleic acids are from a single species, a single cell, two or more organisms, two or more species, or from a population of microbes.

11. The method of claim 1, wherein the sample is a blood sample or bone marrow sample.

12. The method of claim 1, wherein the unique tagged nucleic acid molecules are unique based on a combination of sequence information in the nucleic acid tags and sequence information in the segments of the genomic nucleic acids.

13. The method of claim 12, wherein the nucleic acid tags are six nucleotides long.

14. The method of claim 12, wherein the nucleic acid tags vary in length.

15. The method of claim 12, wherein the nucleic acid tags comprise nucleotide sequences with constant portions and variable portions.

16. The method of claim 15, wherein the length of the constant portions and the length of the variable portions is the same.

17. The method of claim 15, wherein the length of the constant portions and the length of the variable portions are different.

18. The method of claim 15, wherein the variable portions consist of only two species of nucleotides.

19. The method of claim 15, wherein the variable portions consist of only three species of nucleotides.

20. The method of claim 12, wherein the nucleic acid tags comprise variable portions constructed by a set of dinucleotides.

21. The method of claim 12, wherein the nucleic acid tags comprise variable portions constructed by a set of trinucleotides.

22. The method of claim 1, wherein the nucleic acid tags comprise a sufficiently large number of distinct nucleic acid tags.

23. The method of claim 22, wherein the unique tagged nucleic acid molecules are unique based on a combination of sequence information in the nucleic acid tags and sequence information in the segments of the genomic nucleic acids.

24. The method of claim 23, wherein the nucleic acid tags are six nucleotides long.

25. The method of claim 22, wherein the nucleic acid tags vary in length.

26. The method of claim 22, wherein the nucleic acid tags comprise nucleotide sequences with constant portions and variable portions.

27. The method of claim 26, wherein the length of the constant portions and the length of the variable portions is the same.

28. The method of claim 26, wherein the length of the constant portions and the length of the variable portions are different.

29. The method of claim 26, wherein the variable portions consist of only two species of nucleotides.

30. The method of claim 26, wherein the variable portions consist of only three species of nucleotides.

31. The method of claim 22, wherein the nucleic acid tags comprise variable portions constructed by a set of dinucleotides.

32. The method of claim 22, wherein the nucleic acid tags comprise variable portions constructed by a set of trinucleotides.

33. The method of claim 22, wherein the nucleic acid tags comprise nucleotide sequences that are not known before the tagged nucleic acid molecules are generated.

34. The method of claim 22, wherein the nucleic acid tags comprise random nucleotide sequences.

35. The method of claim 22, wherein the nucleic acid tags are substantially unique nucleic acid tags.

36. The method of claim 1, wherein the nucleic acid tags are substantially unique nucleic acid tags.

* * * * *